(12) United States Patent
Zakhary et al.

(10) Patent No.: US 12,245,778 B2
(45) Date of Patent: Mar. 11, 2025

(54) MINIMALLY INVASIVE DISPLACEMENT OSTEOTOMY SYSTEM AND METHOD

(71) Applicant: Wright Medical Technology, Inc., Memphis, TN (US)

(72) Inventors: Beniamin Zakhary, Marietta, GA (US); Gary W. Lowery, Eads, TN (US); Jerry W. West, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 1004 days.

(21) Appl. No.: 16/976,505

(22) PCT Filed: Mar. 28, 2019

(86) PCT No.: PCT/US2019/024587
§ 371 (c)(1),
(2) Date: Aug. 28, 2020

(87) PCT Pub. No.: WO2019/195077
PCT Pub. Date: Oct. 10, 2019

(65) Prior Publication Data
US 2021/0045756 A1 Feb. 18, 2021

Related U.S. Application Data

(60) Provisional application No. 62/652,564, filed on Apr. 4, 2018.

(51) Int. Cl.
*A61B 17/17* (2006.01)

(52) U.S. Cl.
CPC ...... *A61B 17/1775* (2016.11); *A61B 17/1728* (2013.01)

(58) Field of Classification Search
CPC . A61B 17/17; A61B 17/1775; A61B 17/1728; A61B 17/1721; A61B 17/1725;
(Continued)

(56) References Cited

U.S. PATENT DOCUMENTS

| 3,270,416 A | 9/1966 | Anthony et al. |
| 4,931,056 A | 6/1990 | Ghajar et al. |

(Continued)

FOREIGN PATENT DOCUMENTS

| JP | 2004105481 A | 4/2004 |
| JP | 2012515623 A | 7/2012 |

(Continued)

OTHER PUBLICATIONS

First Examination Report issued in connection with corresponding Australian Patent Application No. 2019248528, Nov. 23, 2020, 5 pages.

(Continued)

*Primary Examiner* — Christopher J Beccia
(74) *Attorney, Agent, or Firm* — DUANE MORRIS LLP

(57) ABSTRACT

A cutting guide includes a body extending between an upper surface and a lower surface and defined by a perimeter. The cutting guide further includes a guide foot having a contact surface. A guide element is pivotably coupled to the body. A handle extends from a first end to a second end. The first end is configured to be coupled to the body.

10 Claims, 24 Drawing Sheets

(58) Field of Classification Search
CPC . A61B 17/1742; A61B 17/70; A61B 17/7098; A61B 17/88; A61B 17/86; A61B 17/864
See application file for complete search history.

(56) References Cited

U.S. PATENT DOCUMENTS

| | | | |
|---|---|---|---|
| 5,330,485 | A | 7/1994 | Clayman et al. |
| 5,855,583 | A | 1/1999 | Wang et al. |
| 5,875,782 | A | 3/1999 | Ferrari et al. |
| 6,027,504 | A | 2/2000 | McGuire |
| 6,149,658 | A | 11/2000 | Gardiner et al. |
| 6,159,200 | A | 12/2000 | Verdura et al. |
| 6,267,769 | B1 | 7/2001 | Truwit |
| 6,267,770 | B1 | 7/2001 | Truwit |
| 6,676,706 | B1 | 1/2004 | Mears et al. |
| 6,752,812 | B1 | 6/2004 | Truwit |
| 6,991,627 | B2 | 1/2006 | Madhani et al. |
| 7,491,218 | B2 | 2/2009 | Landry et al. |
| 7,582,091 | B2 | 9/2009 | Duncan et al. |
| 8,083,746 | B2 | 12/2011 | Novak |
| 8,211,112 | B2 | 7/2012 | Novak et al. |
| 2003/0004513 | A1 | 1/2003 | Guzman et al. |
| 2003/0220698 | A1 | 11/2003 | Mears et al. |
| 2006/0052791 | A1* | 3/2006 | Hagen ................. A61B 17/1764 606/86 R |
| 2006/0074430 | A1 | 4/2006 | Deffenbaugh et al. |
| 2009/0076554 | A1 | 3/2009 | Huebner et al. |
| 2010/0191243 | A1 | 7/2010 | Horan et al. |
| 2011/0288552 | A1* | 11/2011 | Acker ................... A61F 2/4605 606/79 |
| 2013/0085500 | A1* | 4/2013 | Meridew ............ A61B 17/1666 606/89 |
| 2014/0142582 | A1 | 5/2014 | Biedermann et al. |
| 2014/0343554 | A1 | 11/2014 | Warnock et al. |
| 2015/0320430 | A1* | 11/2015 | Kehres .................. A61B 17/15 606/87 |
| 2019/0183516 | A1* | 6/2019 | Peterson ............ A61B 17/1757 |
| 2019/0290298 | A1 | 9/2019 | Russell et al. |

FOREIGN PATENT DOCUMENTS

| | | |
|---|---|---|
| JP | 2017527430 A | 9/2017 |
| KR | 1020140062418 A | 3/2014 |
| WO | 2014186404 A1 | 11/2014 |
| WO | 2016039775 A1 | 3/2016 |
| WO | 2017004221 A1 | 1/2017 |

OTHER PUBLICATIONS

Office Action issued in connection with Japanese Patent Application No. 2020-551394, Jan. 11, 2022, 5 pages.
Partial Supplementary Search Report issued in connection with European Patent Application No. 19780571.6, Nov. 26, 2021, 13 pages.
International Search Report and Written Opinion issued in connection with PCT/US2019/024587, Aug. 9, 2019, 19 pages.

* cited by examiner

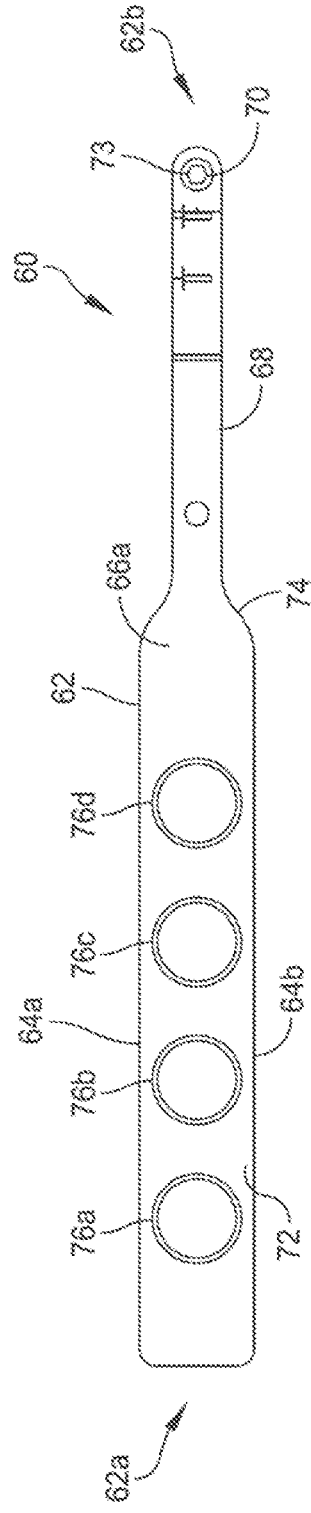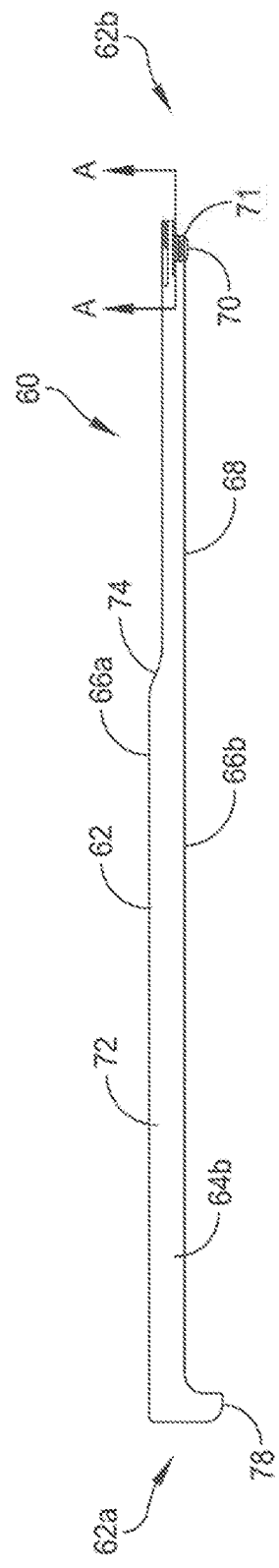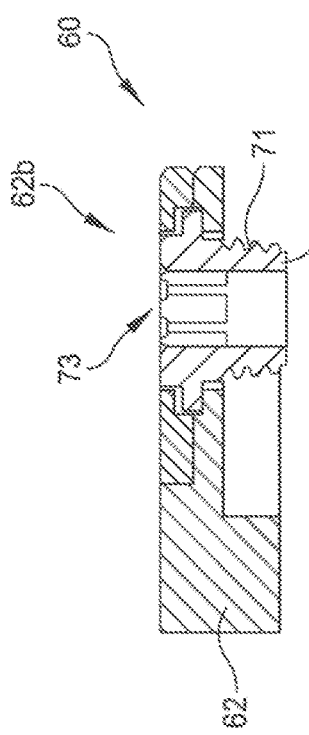

MINIMALLY INVASIVE DISPLACEMENT OSTEOTOMY SYSTEM AND METHOD

CROSS-REFERENCE TO RELATED APPLICATIONS

This application is a National Stage Application, filed under 35 U.S.C. 371, of International Patent Application No. PCT/US2019/024587, filed on Mar. 28, 2019, which claims benefit to U.S. Provisional Application No. 62/652,564, filed on Apr. 4, 2018, and entitled "MINIMALLY INVASIVE DISPLACEMENT OSTEOTOMY SYSTEM AND METHOD," the entireties of which are incorporated by reference herein.

BACKGROUND

Calcaneal displacement osteotomies are used to treat flat foot, Cavus foot, and other foot deformities. A cut is formed in a calcaneus to create a bone fragment that is offset from the remaining calcaneal body in order to correct a deformity. The offset may be made medially to treat flat foot or laterally to treat Cavus foot. Current systems require a large incision or opening to allow formation of the osteotomy, which may cause wound complications post-surgery.

SUMMARY

In various embodiments, a cutting guide is disclosed. The cutting guide includes a body extending between an upper surface and a lower surface and defined by a perimeter. The cutting guide further includes a guide foot having a contact surface. A guide element is pivotably coupled to the body. A handle extends from a first end to a second end. The first end is configured to be coupled to the body.

In various embodiments, a system is disclosed. The system includes a cutting guide and a handle. The cutting guide includes a body extending between an upper surface and a lower surface and defined by a perimeter. The cutting guide further includes a guide foot having a contact surface and a guide element pivotably coupled to the body. The handle includes a body extending from a first end to a second end. The first end is configured to be releasably coupled to the body of the cutting guide.

In various embodiments, a method is disclosed. The method includes a step of positioning a cutting guide adjacent to a first bone. The cutting guide includes a body extending between an upper surface and a lower surface and defined by a perimeter. The cutting guide further includes a guide foot having a contact surface and a guide element pivotably coupled to the body. A cutting instrument is inserted through a channel defined by the guide element and a cut is formed in the first bone by pivoting the guide element and the cutting instrument with respect to the body. The cutting instrument traverses a plane having an angle with respect to the upper surface of the cutting guide.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 6 illustrates a top view of a plate inserter, in accordance with some embodiments.

FIG. 7 illustrates a side view of the plate inserter or FIG. 6, in accordance with some embodiments.

FIG. 8 illustrates a cross-section taken along line A-A in FIG. 7, in accordance with some embodiments.

DETAILED DESCRIPTION

Figure 2:
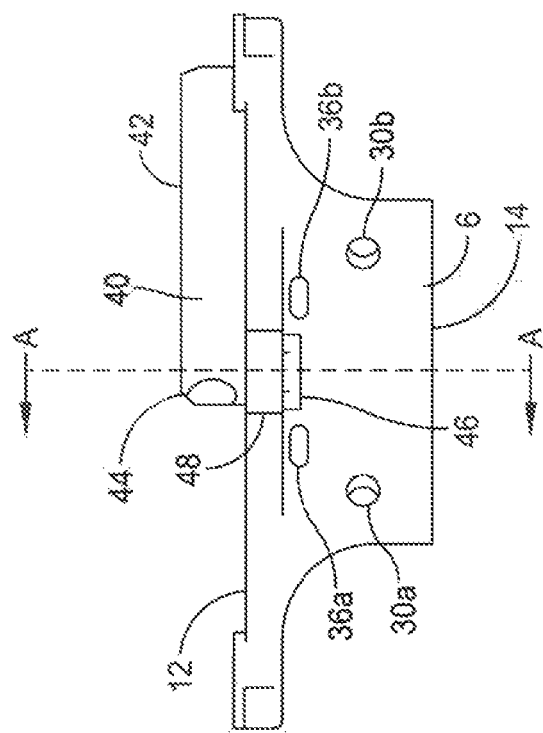
FIG. 2 illustrates a side view of the cutting guide of FIG. 1, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a system for performing a minimally invasive procedure is disclosed. The system includes a cutting guide. The cutting guide is configured to be positioned adjacent to a first bone, such as a calcaneus. The cutting guide is configured to releasably couple to a handle. The handle is configured to assist in positioning of the cutting guide prior to temporarily fixing the position of the cutting guide using one or more fixation devices. The handle can be removed from the cutting guide. The cutting guide includes a pivoting guide portion defining a channel sized and configured to receive a cutting instrument therethrough. The cutting instrument can include a burr. The cutting instrument is inserted through the pivoting guide portion and pivoted to form a cut or osteotomy in the first bone. After forming the cut in the first bone, the cutting instrument, cutting guide, and fixation devices are removed. A plate is positioned between a first portion and a second portion of the bone formed by the cutting instrument. The plate can be positioned by a plater inserter. The plate is coupled to the bone to maintain the position of the first portion and the second portion of the bone.

In various embodiments, a method of forming an osteotomy is disclosed. The method includes a step of forming a first incision at a surgical site adjacent to a first bone. A cutting guide is positioned at the first incision. The cutting guide is configured to releasably couple to a handle. The handle is configured to assist in positioning the cutting guide adjacent to the first incision. The cutting guide is temporarily fixed to the first bone by at least one temporary fixation device. The handle is removed from the cutting guide. A cutting instrument is inserted through a channel defined by a pivoting guide of the cutting guide. A cut is formed in the first bone by pivoting the cutting guide to move the cutting instrument in a predetermined arc. The cutting guide, cutting instrument, and temporary fixation elements are removed from the surgical site. A second incision is formed at the surgical site and a plate is inserted adjacent to the first bone. The plate is coupled to a first portion of the bone and a second portion of the bone defined by the cut. The plate can be positioned by a plate inserter.

Figure 1:
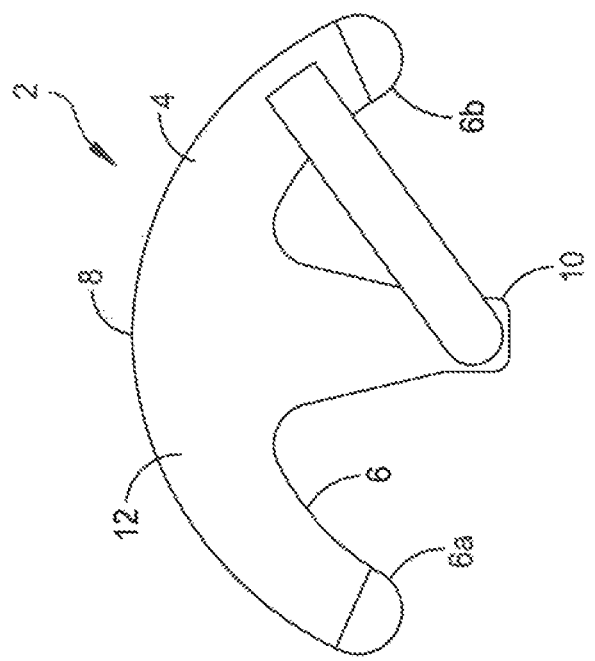
FIG. 1 illustrates a top view of a cutting guide, in accordance with some embodiments.
Figure 3:
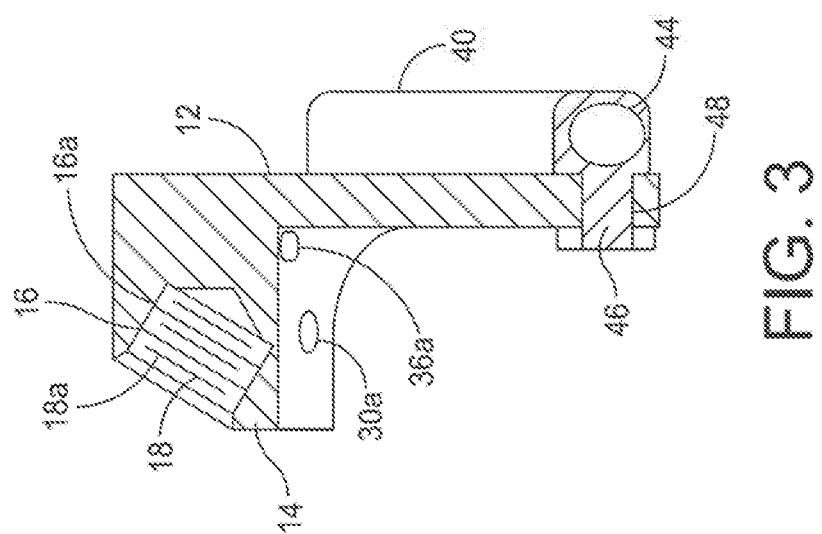
FIG. 3 illustrates a cross-sectional view taken along line A-A in FIG. 2, in accordance with some embodiments.

FIGS. 1-3 illustrate a cutting guide 2, in accordance with some embodiments. The cutting guide 2 includes a body 4 extending between a front edge 6 and a rear edge 8 and extending between an upper surface 12 and a lower surface 14. The rear edge 8 of the body 4 defines an arcuate surface. The front edge 6 defines an arcuate surface similar to the arcuate surface of the rear edge 8. The arcuate surface of the front edge 6 includes a guide foot 10 extending from a middle of the arcuate surface such that the front edge 6 defines a first arcuate surface 6a and a second arcuate surface 6b separated by the guide foot 10. The guide foot 10 includes a contact surface 16. The contact surface 16 extends perpendicular to the upper surface 12 of the body 4 and is configured to abut or contact a bone, skin surface, or other surgical site. In some embodiments, the guide foot 10 defines a midpoint of the cutting guide 2.

Figure 4:
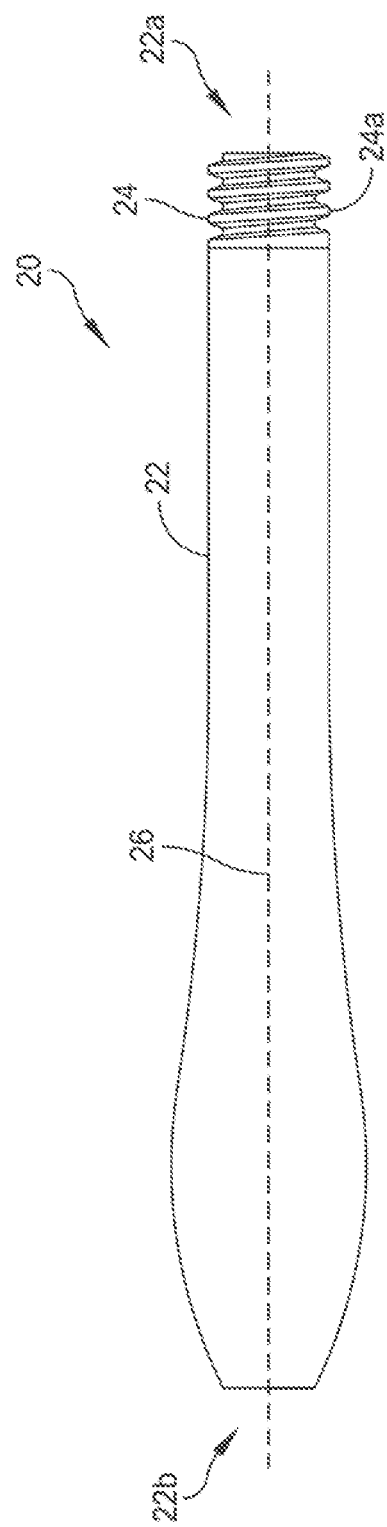
FIG. 4 illustrates a handle configured to be releasably coupled to the cutting guide of FIG. 1, in accordance with some embodiments.

The body 4 is configured to releasably couple to a handle 20, such as the handle 20 illustrated in FIG. 4. For example, in the illustrated embodiment, the handle 20 is configured to releasably couple to the lower surface 14 of the body 4, although it will be appreciated that the handle 20 can be releasably coupled to any portion of the body 4. For example, in various embodiments, the body 4 can include a coupling element at one or more of the upper surface 12, the lower surface 14, the rear wall 8, the front edge 6, and/or any other portion of the body 4. The coupling element is configured to releasably couple the handle 20 to the body 4. The coupling element can include any suitable coupling element, such as a hole, slot, extensions, insert, and/or any other suitable coupling element formed in and/or on the body 4 and a complementary coupling element formed on and/or in the handle 20.

Figure 11:
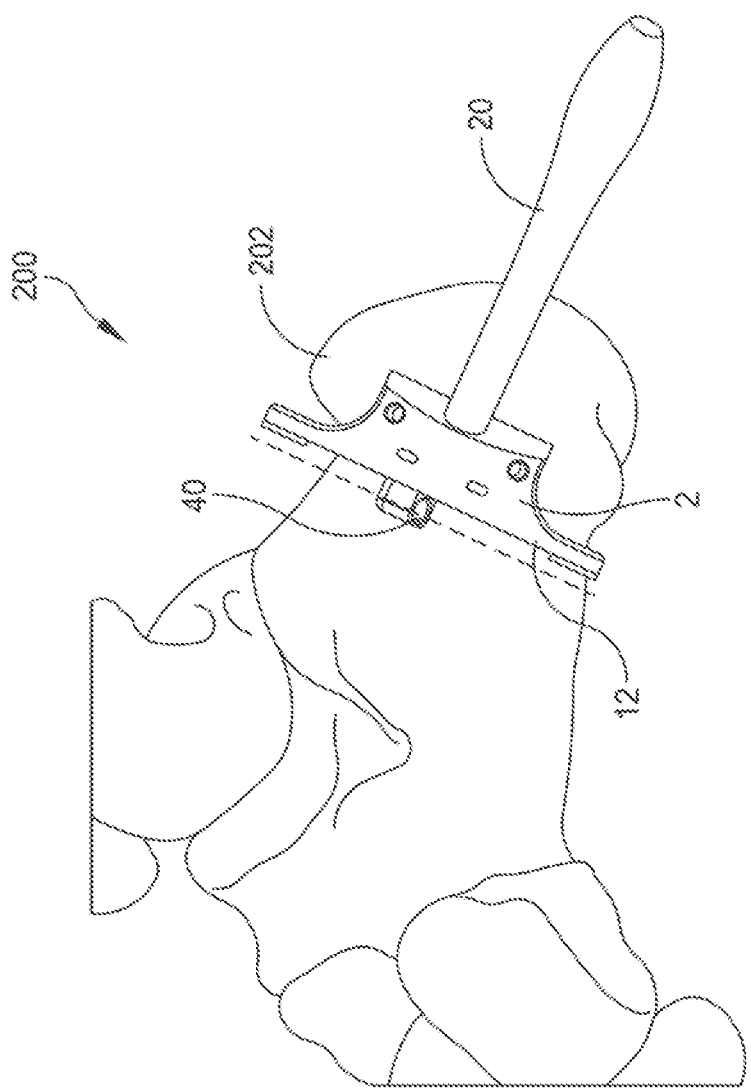
FIG. 11 illustrates a cutting guide and attached handle positioned adjacent to a first bone, in accordance with some embodiments.

The handle 20 is configured to be coupled to the body 4 to allow a surgeon (or other user) to position the cutting guide 2 adjacent to a surgical site, as described in greater detail below with respect to FIG. 11. The handle 20 is coupled to and extends from the body 4. A surgeon (or other user) can manipulate the handle 20 to position the body 4 adjacent to the surgical site. The cutting guide 2 may be temporarily fixed with respect to the surgical site using one or more temporary fixation devices, as discussed in greater detail below.

In some embodiments, the coupling element includes a hole 16 sized and configured to receive a portion of the handle 20. In some embodiments, the hole 16 can include a coupling feature 18 configured to releasably couple the handle 20 to the body 4. For example, in some embodiments, the hole 16 includes at least one thread extending about an inner circumference of the hole 16 and the handle 20 includes a matching thread 24a extending over a portion of the outer surface of the handle 20, such as a distal portion 22a. Although embodiments are illustrated including threads, it will be appreciated that any suitable coupling element can be used. For example, in various embodiments, the handle 20 and/or the body 4 may include a lug, a cross-pin, a setscrew, a ball seal, one or more ball plungers, living hinge or snap features, buckles, cams, springs, collet mechanism, snap rings, dovetail, T slot, or tongue and groove feature, opposable magnets, and/or any other suitable coupling mechanisms.

In some embodiments, the handle 20 includes a body 22 extending from a distal end 22a to a proximal end 22b. In the illustrated embodiment, the handle 20 extends generally along a longitudinal axis 26, although it will be appreciated that the handle 20 may be curved, angled, and/or otherwise non-linear. The handle 20 includes a coupling portion 24 configured to couple the handle 20 to the body 4 of the cutting guide 2. In some embodiments, the coupling portion 24 includes a complementary coupling element with respect to a coupling element 16 formed on and/or in the body 4. For example, in some embodiments, the body 4 includes a hole 16 having a female thread 18a extending about an inner circumference of the hole 16. The handle 20 includes a complementary coupling element in the form of a male thread 24a formed about a distal end 22a of the body 22. The male thread 24a is complementary to and configured to couple to the female thread 18a within the hole 16a.

Figure 25:
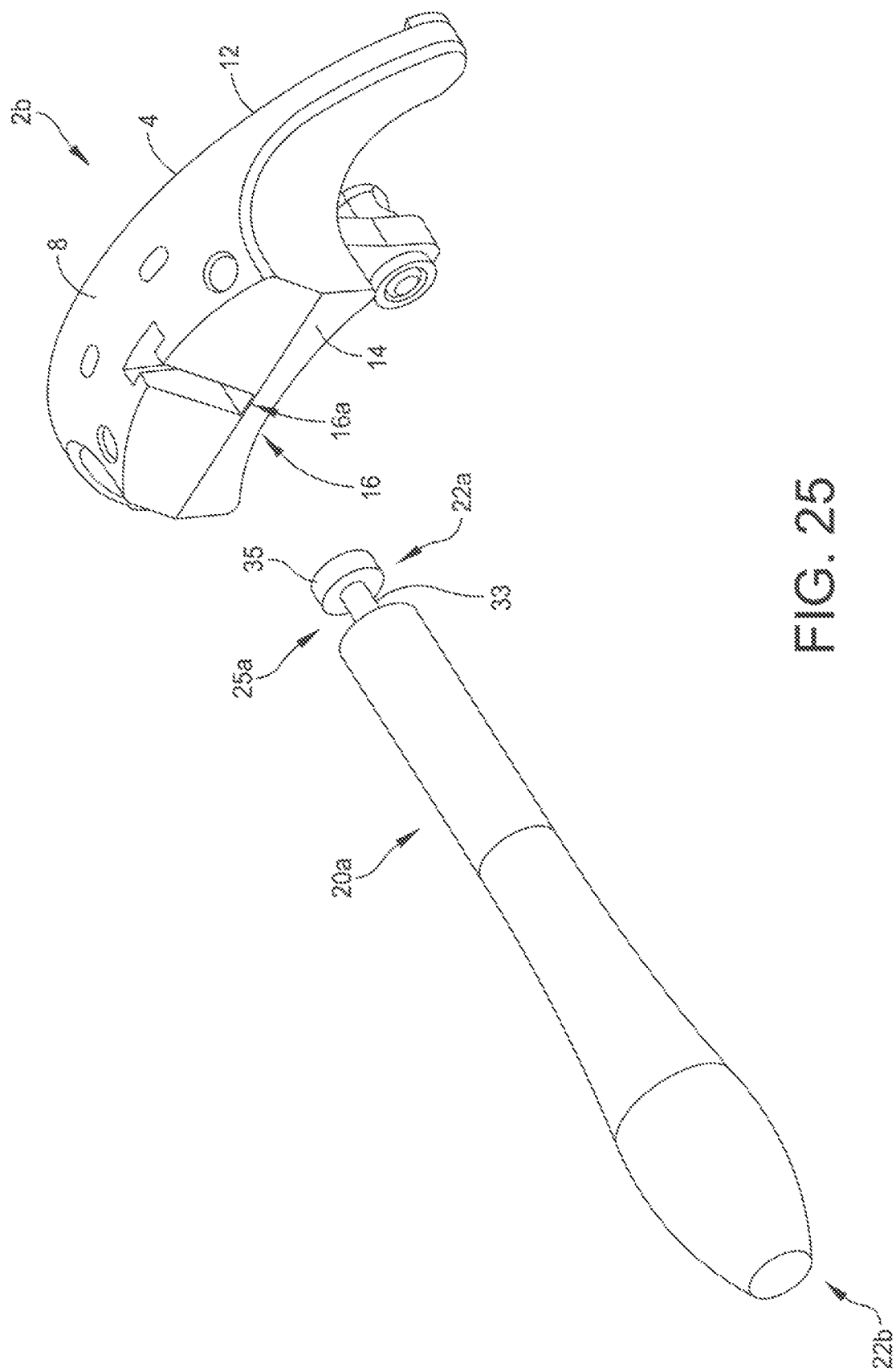
FIG. 25 illustrates an isometric view of a cutting guide and handle having a T-slot handle coupling mechanism, in accordance with some embodiments.
Figure 26:
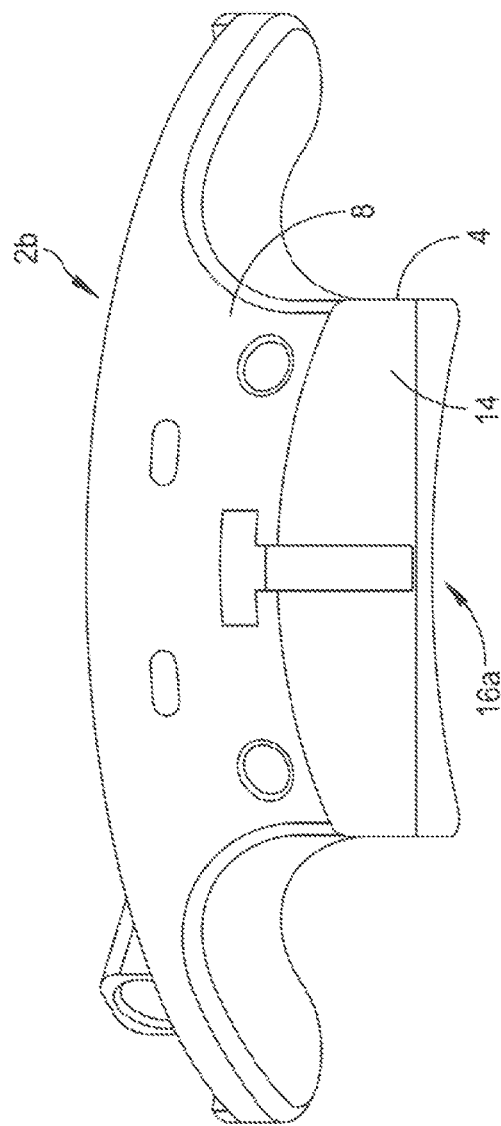
FIG. 26 illustrates an isometric bottom view of the cutting guide of FIG. 25, in accordance with some embodiments.
Figure 27:
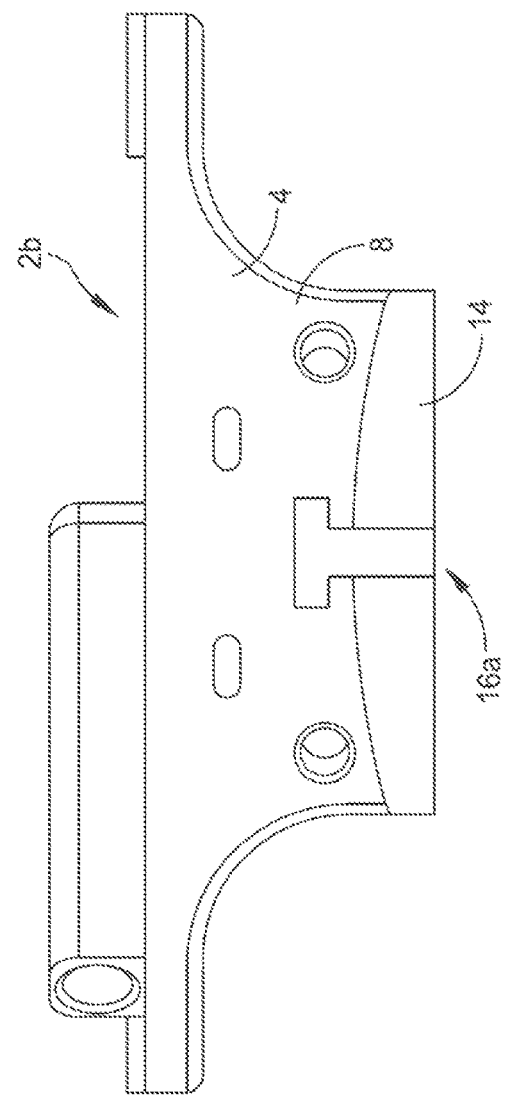
FIG. 27 illustrates a side view of the cutting guide of FIG. 25, in accordance with some embodiments.

In some embodiments, for example as shown in FIGS. 25-27, the coupling element 16 formed on the body 4 of the cutting guide 2b includes a slot 16a extending over at least a portion of the body 4. In the illustrated embodiment, the slot 16a includes a T-slot extending from a rear edge 8 into the body 4, although it will be appreciated that the T-slot 16a can extend from any suitable surface of the cutting guide 2, such as the rear surface 8, the upper surface 12, the lower surface 14, etc. The T-slot 16a extends through the lower surface 14 of the cutting guide 2 such that a handle 20a coupled to the T-slot 16a extends proximally from the lower surface 14.

In some embodiments, the handle 20a includes a complimentary T-bolt head 25a configured to be inserted into and coupled to the T-slot 16a defined in the body 4. The T-bolt head 25a includes a shaft 33 extending distally from a distal end 22a of the handle 20a and a head element 35 coupled to a distal end of the shaft 3. The head element is sized and configured to be received within a first portion of the T-slot 16a and the shaft 33 is sized and configured to be received within a second portion of the T-slot 16a. The T-slot 16a can include an indent or other fixation point to fix the position of the handle 20, the T-slot 16a can be sized for friction engagement with the T-bolt head 25a, and/or the handle 20 can include a tightening and/or other locking mechanism to couple the handle 20 to the body 4 at a fixed position. Although embodiments are discussed herein including a T-slot 16a, it will be appreciated that the slot and complementary coupling element can include any suitable shape.

Figure 28:
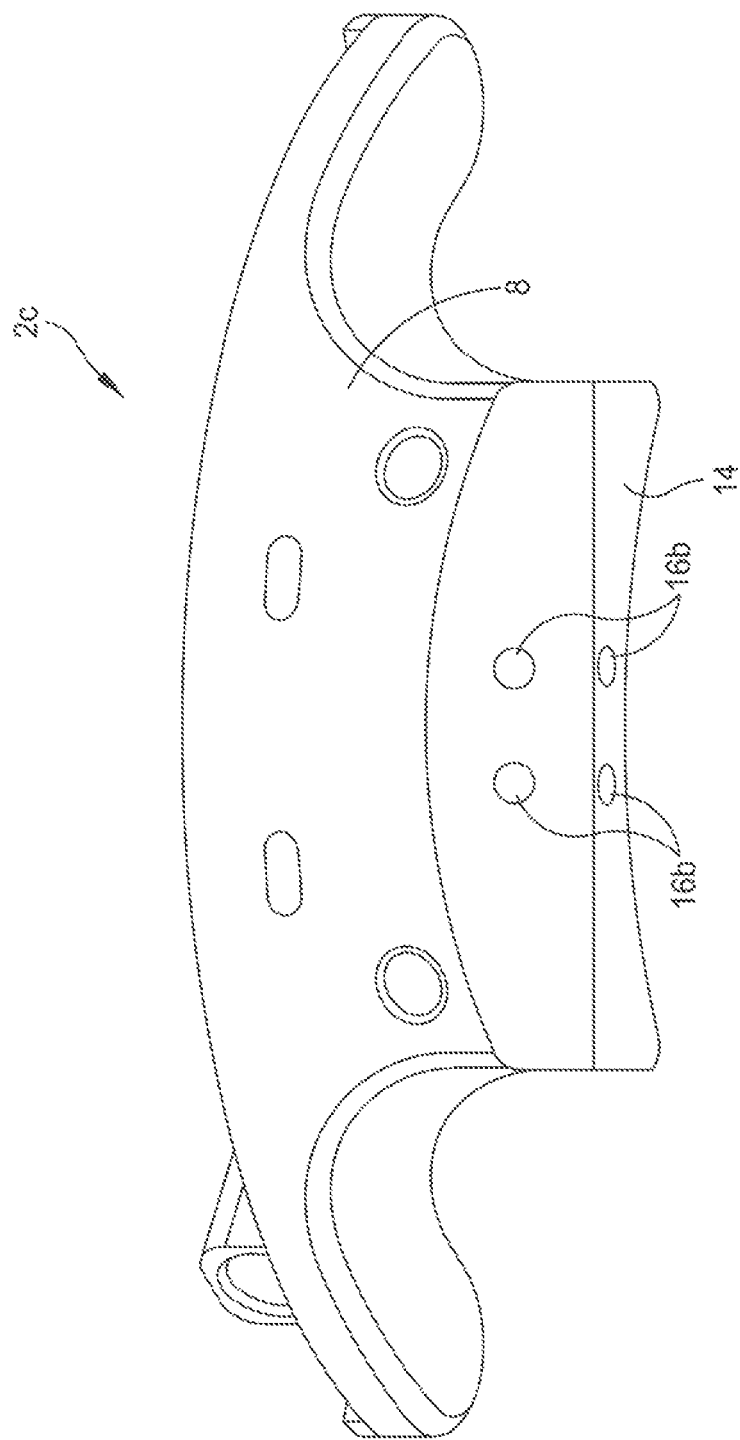
FIG. 28 illustrates a bottom isometric view of a cutting guide including a plurality of coupling holes extending from a bottom surface, in accordance with some embodiments.
Figure 29:
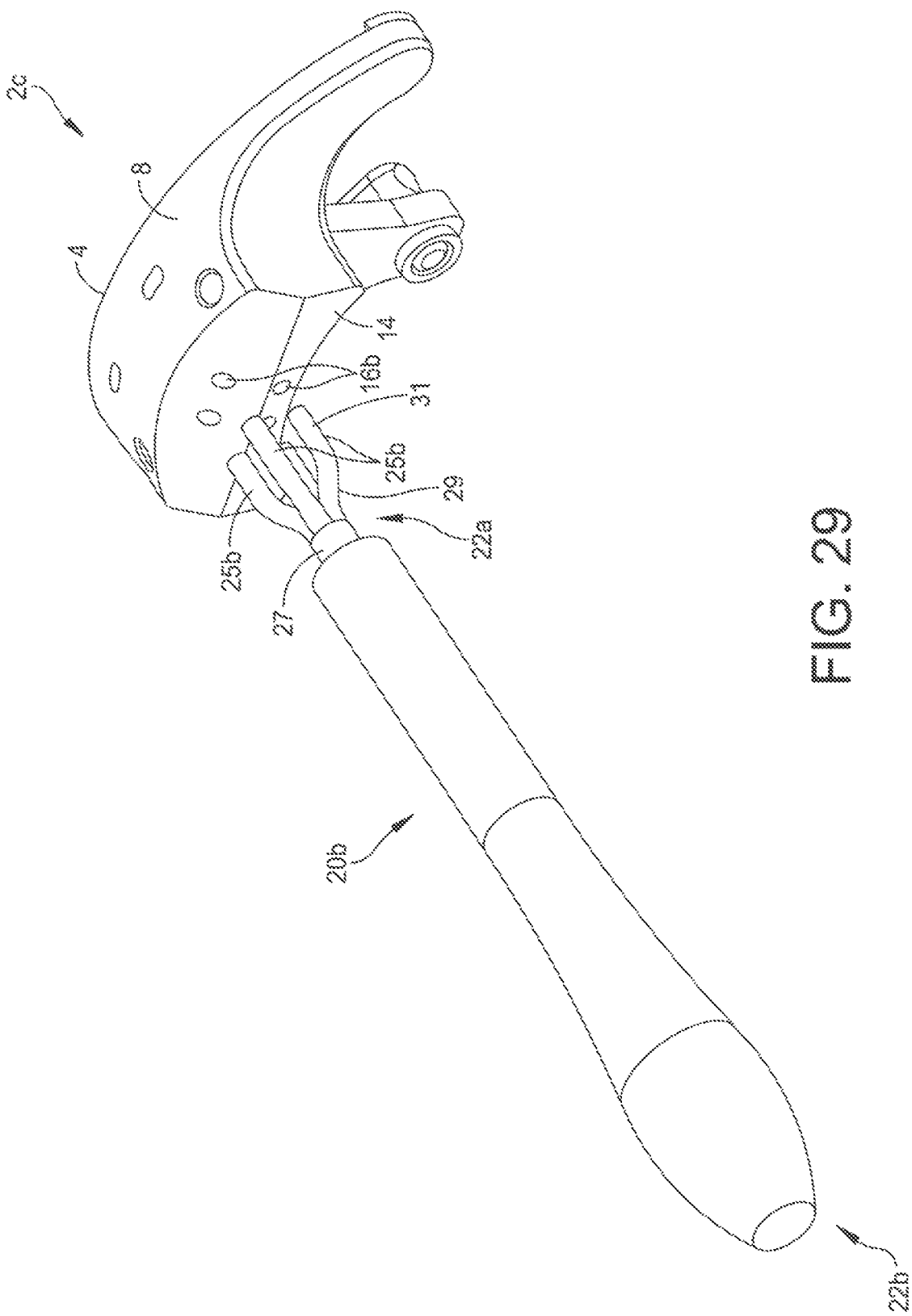
FIG. 29 illustrates the cutting guide of FIG. 28 adjacent to a handle including a plurality of prongs configured to couple the handle to the coupling holes formed in the cutting guide, in accordance with some embodiments.

In some embodiments, for example as shown in FIGS. 28-29, the coupling element 16 formed on the body 4 of the cutting guide 2c includes a plurality of coupling holes (or channels) 16b sized and configured to receive a complimentary coupling element 25b formed on a handle 20b. In the illustrated embodiment, each of the plurality of coupling holes 16b extend into the body 4 from a lower surface 14, although it will be appreciated that one or more of the coupling holes 16b can extend from any suitable surface, such as a rear surface 8, upper surface 12, lower surface 14, etc. The coupling holes 16b can extend partially and or fully (e.g., formed as channels) towards an opposite side of the body 4. The coupling holes 16b are formed in the body 4 at a predetermined angle with respect to upper surface 12 of the body 4.

In some embodiments, a handle 20b includes a plurality of prongs 25b extending from a distal end 22b of the handle body 22. The plurality of prongs 25b are positioned such that each of the prongs 25b is complimentary to a coupling hole 16b formed in the body 4 of the cutting guide 2. Each of the plurality of prongs 25b has a diameter sized and configured for an interference (e.g., press-fit or friction engagement) coupling with an interior surface of a complimentary coupling hole 16b. In the illustrated embodiment, each of the prongs 25b extend from a common base 27 and include an offset portion 29 and a coupling portion 31. In some embodiments, each of the prongs 25b can be coupled directly to the handle body 22, can include additional offset portions, and/or can omit the offset portion 29. In the illustrated embodiment, the coupling portion 31 includes a first diameter and the offset portion 29 includes a second diameter less than the first diameter, although it will be appreciated that the first diameter can be less than the second diameter, greater than the second diameter, or equal to the second diameter.

Figure 30:
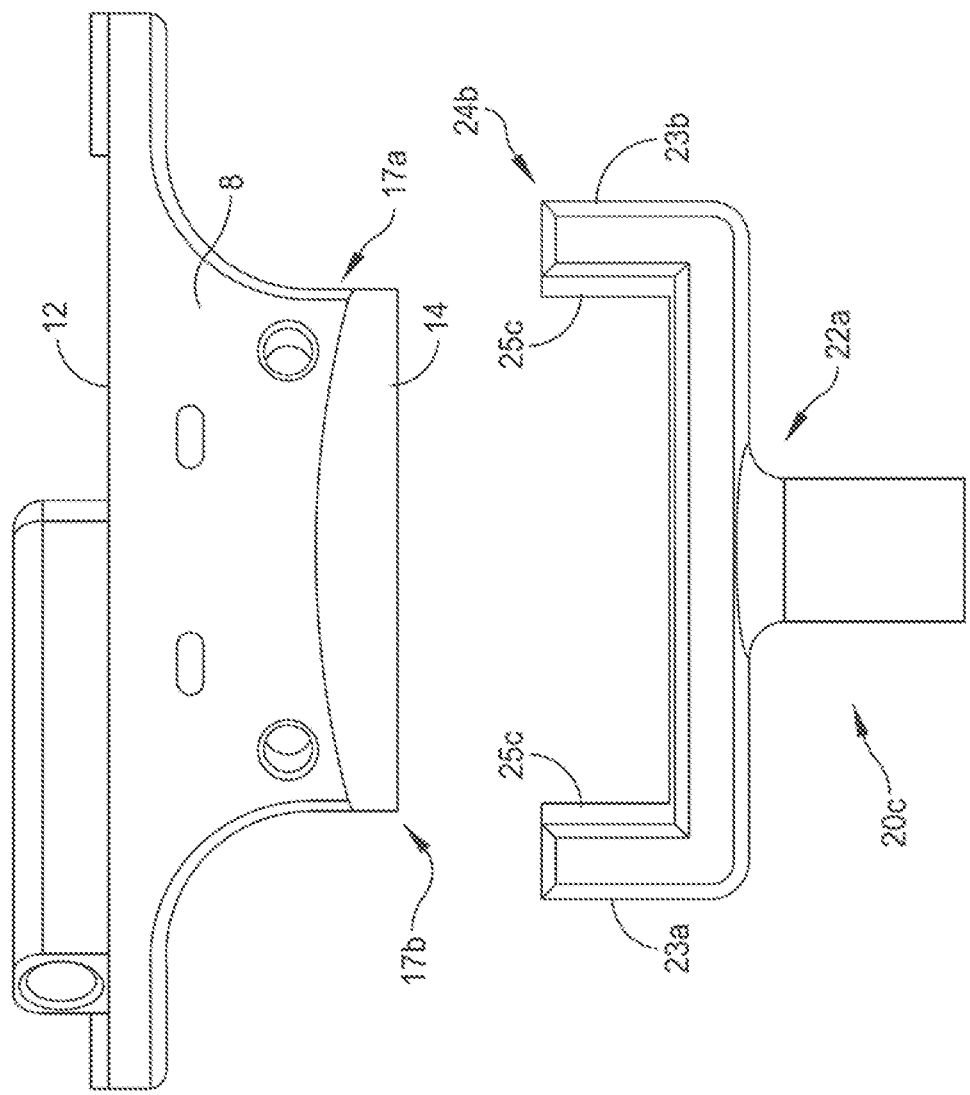
FIG. 30 illustrates a side view of a cutting guide and a handle having a slot coupling mechanism, in accordance with some embodiments.
Figure 31:
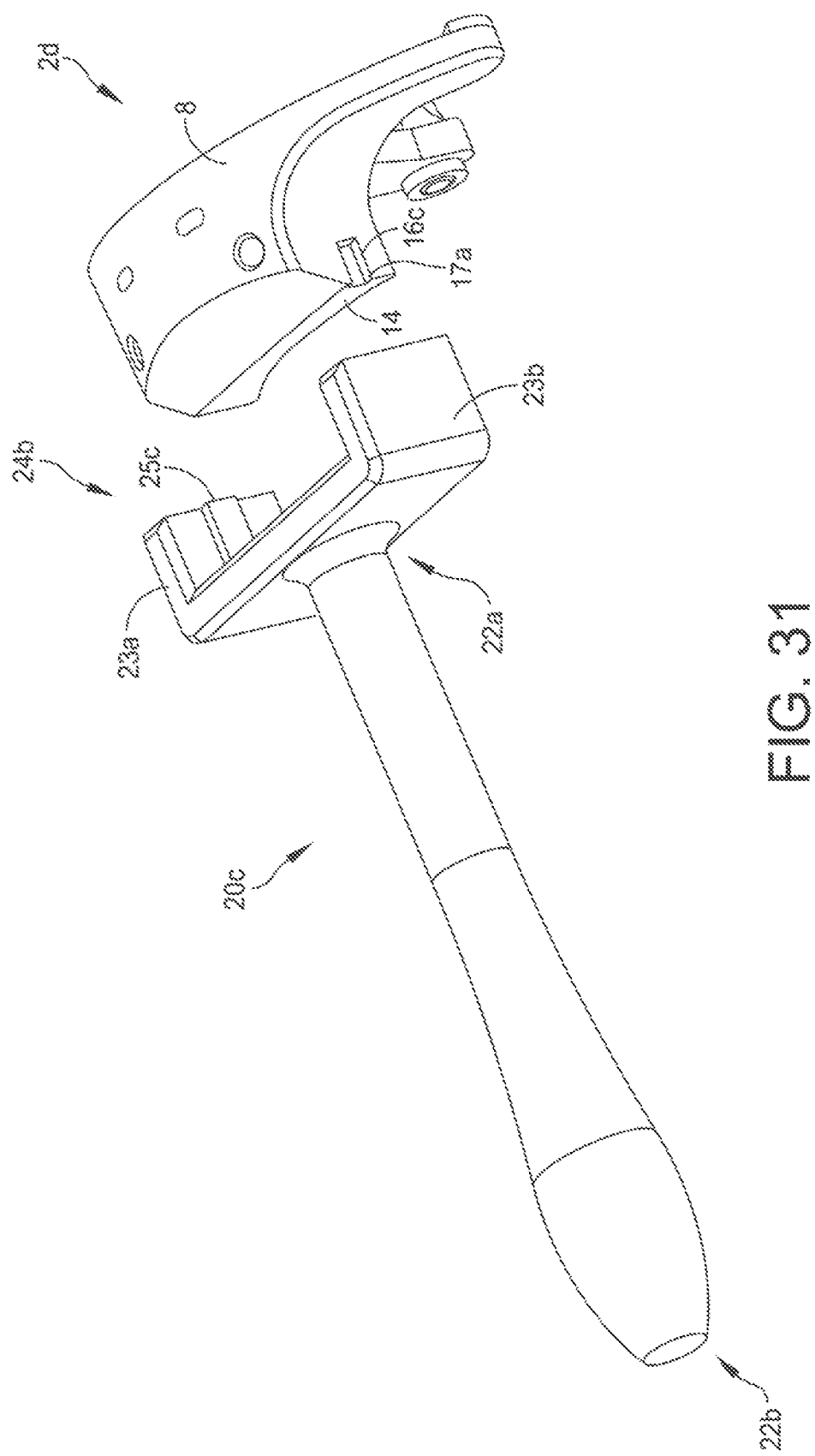
FIG. 31 is an isometric view of the cutting guide and handle of FIG. 30, in accordance with some embodiments.

In some embodiments, for example as shown in FIGS. 30-31, the coupling element 16 formed on the body 4 of the cutting guide 2 includes a plurality of slots 16c sized and configured to receive a complimentary coupling tab 25c formed on a handle 20c. Each of the plurality of slots 16c extend from a first surface of the body 4 along a second surface. For example, in the illustrated embodiment, a first slot 17a extends from a lower surface 14 of the body along a first side of the rear surface 8 and a second slot 17b extends from the lower surface 14 along a second side of the rear surface 8. Although specific embodiments are discussed herein, it will be appreciated that the slots can be formed on any surface of the body 4.

In some embodiments, a handle 20c includes a coupling element 24 including a gripping head 24b configured to wrap around and/or otherwise contain a portion of the body 4. For example, in the illustrated embodiment, the gripping head 24b is sized and configured to interface with a peripheral edge (e.g., rear edge 8) of the body 4 and to receive the body 4 between a first prong 23a and a second prong 23b of the gripping head 24b. A plurality of tabs 25c extend from an inner surface of the gripping head 24b. Each of the plurality of tabs 25c is sized and configured to be inserted into one of the plurality of slots 16c when the body 4 is positioned within the gripping head 24b. In the illustrated embodiment, a first tab 16c extends from the first prong 23a and a second tab 16c extends from the second prong 23b.

In some embodiments, the body 4 defines a plurality of fixation holes 30a, 30b extending therethrough. The fixation holes 30a, 30b define channels extending through the body 4 from the front edge 6 to the rear edge 8. The fixation holes 30a, 30b can extend through the body 4 on parallel and/or non-parallel axes. In some embodiments, the axis of a first fixation hole 30a and the axis of a second fixation hole are offset from a center longitudinal axis of the body 4 by equal and/or opposite angles.

The fixation holes 30a, 30b are sized and configured to receive temporary fixation elements therethrough. The temporary fixation elements are configured to couple the cutting guide 2 to the first bone. The temporary fixation elements can be any suitable fixation element, such as a k-wire, a screw, a threaded pin, small clip, a strap, a nail, and/or any other suitable fixation device. Although embodiments are illustrated with two fixation holes 30a, 30b, it will be appreciated that the body 4 can define any suitable number of fixation holes, such as one, two, three, four, etc. In some embodiments, a subset of the fixation holes 30a, 30b can be used based on positioning of the cutting guide 2.

In some embodiments, the body 4 defines one or more guide holes 36a, 36b extending therethrough. The guide holes 36a, 36b are configured to provide alignment indicators for one or more imaging techniques, such as fluoroscopic imaging. The guide holes 36a, 36b are configured to provide an alignment indicator with respect to at least a first bone when the cutting guide 2 is positioned at a surgical site. The guide holes 36a, 36b may extend through the body 4 at any suitable angle, such as, for example, parallel to a plane defined by the upper surface 12 of the body 4, parallel to a longitudinal axis of a guide element 40, perpendicular to an intended osteotomy line, and/or at any other suitable angle.

In some embodiments, a guide element 40 is pivotably coupled to the body 4. In the illustrated embodiment, the guide element 40 is pivotably coupled to a distal portion of the extension 10, although it will be appreciated that the guide element 40 can be pivotably coupled to any portion of the body 4. The guide element 40 includes a body 42 defining a channel 44 extending from a first end to a second end. The channel 44 is sized and configured to receive a cutting instrument therein. In some embodiments, the body 42 is a longitudinal body extending from the first end to the second end along a longitudinal axis, although it will be appreciated that the body 42 can define any suitable shape, such as a curved, linear, and/or other shape extending from a first opening to a second opening.

The body 42 is pivotably coupled to the body 4 of the cutting guide 2 by a pivoting element 46. In some embodiments, the pivoting element 46 includes a pin 46a extending from the longitudinal body 42 along an axis orthogonal to the channel 44. The pin 46a is received within a hole 48 defined in the body 4. The pin 46a may be locked or otherwise permanently coupled to the body 4 such that the guide element 40 can pivot with respect to the body 4 in a first plane and is otherwise fixed with respect to the body 4 and/or may be freely moveable in one or more axes. In some embodiments, the body 42 is pivotably coupled to the body 4 by a ball and socket (or other socket connection) configured to allow rotation of the pivoting guide 40 in at least one axis with respect to the body 4.

In some embodiments, the upper surface 12 of the body 4 defines a plane having a predetermined angle with respect to a plane defined by pivoting of the pivoting guide 40. For example, in some embodiments, the upper surface 12 of the body 4 defines a plane parallel with a plane traversed by the pivoting guide 40 when the pivoting guide 40 is pivoted about the pivot point. In other embodiments, the upper surface 12 can define a plane at a predetermined angle with respect to the plane traversed by the pivoting guide 40 when the pivoting guide 40 is pivoted about the pivot point. The upper edge 12 can provide a visual indication to a surgeon or other user regarding a position of a cut to be made in the first bone.

Figure 5:
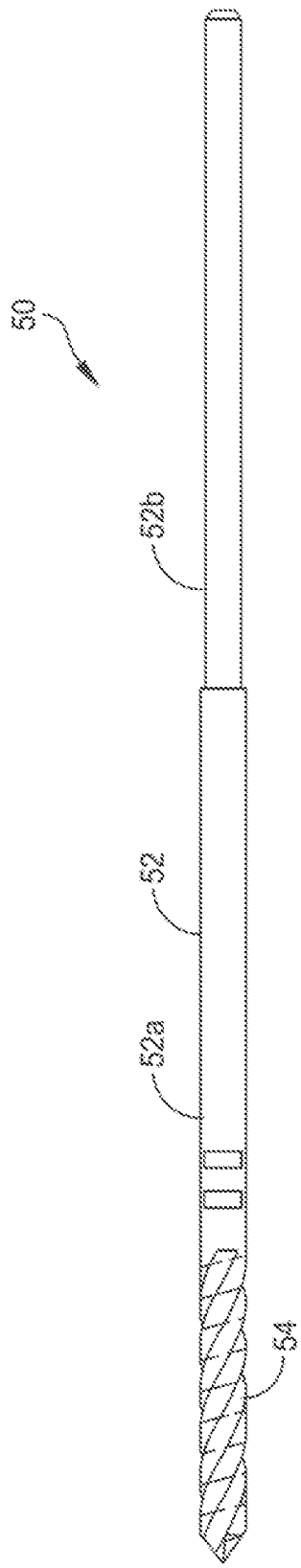
FIG. 5 illustrates a cutting instrument sized and configured to be received within a portion of the cutting guide of FIG. 1, in accordance with some embodiments.

In some embodiments, the channel 44 defined by the guide element 40 is sized and configured to receive a cutting element, such as the cutting element 50 illustrated in FIG. 5. The cutting element 50 includes a body 52 extending generally along a longitudinal axis. The body 52 defines a cutting portion 54 extending over a portion of the body 52 adjacent to a distal end. The cutting portion 52 can define a burr, blade, drill, reamer, endmill, saw, and/or any other suitable cutting instrument. In some embodiments, the cutting portion 54 has a predetermined length sufficient to form an osteotomy in the first bone when the cutting instrument 50 is inserted through and pivoted by the pivoting guide 40.

In some embodiments, the body 52 of the cutting element 50 includes a first portion 52a having a first diameter and a second portion 52b having a second diameter. The cutting portion 54 extends partially over the first portion 52a. In some embodiments, the first diameter is greater than, or different than, the second diameter. The first portion 52a is sized and configured to be received within the channel 44 defined by the pivoting guide 40. In some embodiments, the first diameter is approximately equal to an internal diameter of the channel 44. The first portion 52a is configured to have a close fit with the channel 44 to prevent movement of the cutting instrument 50 within the pivoting guide 40 during a cutting procedure. The second portion 52b is sized and configured to couple the cutting element 50 to a driver.

FIGS. 6-8 illustrate a plate inserter 60 configured to position a bone plate, in accordance with some embodiments. The plate inserter 60 includes a body 62 extending generally along a longitudinal axis from a proximal end 62a to a distal end 62b. The body 60 extends between parallel longitudinal edges 64a, 64b, a top edge 66a, and a bottom edge 66b. An inserter portion 68 is positioned adjacent to a distal end 62b of the body 62. The inserter portion 68 has a first width extending from the first longitudinal edge 64a to the second longitudinal edge 64b and a first thickness extending from the top edge 66a to the bottom edge 66b. The inserter portion 68 is sized and configured for insertion to a surgical site, for example, including a first bone having an osteotomy formed by a cutting instrument 50 inserted through a cutting guide 2.

The inserter portion 68 includes a plate fixation element 70 located adjacent a distal end 62b. The plate fixation element 70 is sized and configured to temporarily couple the inserter portion 68 to a bone plate, such as the bone plate 80 discussed in greater detail with respect to FIG. 9. For example, in some embodiments, the plate fixation element 70 includes a bolt or screw 71 rotatable within the insert portion 68. The screw 71 is sized and configured to be received within a hole defined by a bone plate to couple the inserter portion 68 to the plate 80. The plate fixation element 70 can define threads, ridges, and/or any other locking feature configured to couple the fixation element 70 to the bone plate. In some embodiments, the temporary fixation element defines a central hole 73 extending along a longitudinal axis to allow passage of an instrument, such as a drill bit, therethrough.

In some embodiments, the plate inserter 60 includes a handle portion 72 having a second width extending from the first longitudinal edge 64a to the second longitudinal edge 64b and a second thickness extending from the top edge 66a to the bottom edge 66b. In some embodiments, the second width is greater than the first width and/or the second thickness is greater than the first thickness. A transition portion 74 defines a tapered neck between the inserter portion 68 and the handle portion 72. The transition portion 74 tapers from the first thickness and the first width at a first end 74a coupled to the inserter portion 68 to the second thickness and the second width at a second end 74b coupled to the handle portion 72. In some embodiments, the transition portion 74 is omitted and the plate inserter 60 includes an abrupt transition from the first thickness and/or first width of the inserter portion 68 to the second thickness and/or second width of the handle portion 72. It is also envisioned that the transition portion 74 may be omitted and the first thickness/width and the second thickness/width are similar.

In some embodiments, the handle portion 72 defines a plurality of holes 76a-76d extending from the top edge 66a to the bottom edge 66b. The holes 76a-76d are configured to facilitate sterilization and reduce weight of the plate inserter 60. Although four holes 76a-76d are illustrated, it will be appreciated that the handle portion 72 and/or the inserter portion 68 can include any suitable number of through holes. In some embodiments, the plate inserter 60 may include one or more additional weight saving and/or sterilization features, such as channels, slots, grooves, reduced thicknesses, etc.

In some embodiments, a stop 78 extends from a distal end 62a of the handle portion 72. The stop 78 is sized and configured to provide a physical stop or indication for a user holding the plate inserter 60. The stop 78 can extend from the top edge 66a and/or the bottom edge 66b of the plate inserter 60. The stop 78 may define a curved and/or linear surface that extends at a predetermined angle from the respective edge 66a, 66b. The stop 78 is configured to prevent slippage of the plate inserter 60 during an insertion process.

Figure 9:
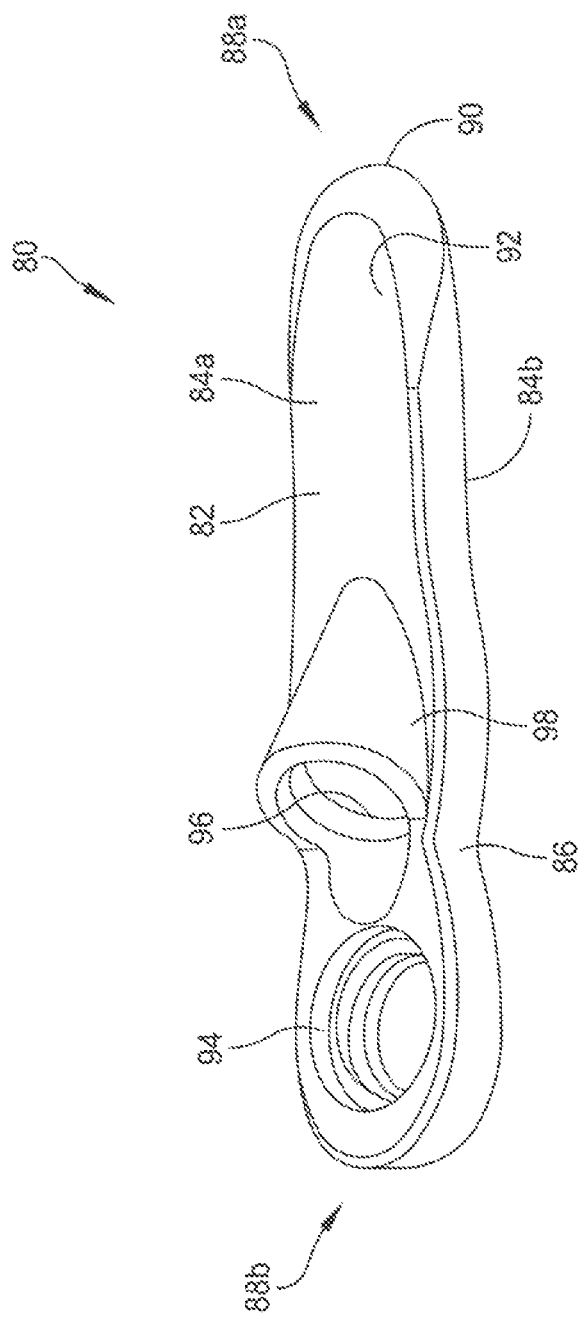
FIG. 9 illustrates a bone plate configured to be coupled to a first bone, in accordance with some embodiments.

FIG. 9 illustrates a bone plate 80 configured to couple to the plate inserter 60, in accordance with some embodiments. The bone plate 80 includes a body 82 extending between a top surface 84a and a bottom surface 84b and defined by a perimeter wall 86. In the illustrated embodiment, the perimeter wall 86 defines a generally oblong shape, although it will be appreciated that any suitable shape, such as rectangular, circular, oblong, etc. can be defined by the perimeter wall 86.

A distal end 88a of the body 82 defines an insertion edge 90. The insertion edge 90 defines a chamfer that facilitates insertion of the bone plate 80 into a second portion of a bone, as described in greater detail below with respect to FIGS. 11-19. An insertion portion 92 of the body 82 is positioned adjacent to the distal end 88a of the bone plate 80. The insertion portion 92 is sized and configured for insertion into the second portion of the bone. The insertion portion 92 can extend over any predetermined portion of the body 82 (or bone), such as, for example, half of the body 82, a quarter of the body 82, and/or any other portion of the body 82.

In some embodiments, a first fastener hole 94 extends from a top surface 84a to a bottom surface 84b of the body 82. The first fastener hole 94 is positioned adjacent to a proximal edge 88b of the body 82. The first fastener hole 94 can extend through the body 82 at a predetermined angle with respect to the top surface 88a and/or the bottom surface 88b. For example, in the illustrated embodiment, the first fastener hole 94 extends through the body 82 perpendicular to the top and bottom surfaces 88a, 88b, although it will be appreciated that the fastener hole 94 can extend through the body 82 at a non-perpendicular angle. In some embodiments, the fastener hole 94 defines a polyaxial locking hole configured to receive a locking fastener, such as a locking screw, therein. The first fastener hole 94 is configured to align a fastener inserted therein with a first portion of a bone, as described in greater detail below.

In some embodiments, the bone plate 80 includes an angled second fastener hole 96 including a hole shroud 98. The hole shroud 98 extends from the top surface 88a of the bone plate 80 and defines an arc or portion of a cylinder raised above the top surface 88a of the body 82. The hole shroud 98 is configured to shroud the head of a fastener received in the second fastener hole 96. The hole shroud 98 can be further configured to provide support and/or compression within a portion of a bone, such as the second portion, into which the hole shroud 98 projects. In some embodiments, the second fastener hole is an angled non-locking fastener hole extending through the body 82 of the bone plate 80. The non-locking fastener hole is configured to receive a compression fastener therein configured to extend into a second portion of a bone, as described in greater detail below. Additional description and embodiments of a bone plate are described in U.S. Pat. No. 8,986,353, entitled "Osteotomy Plate, Plate Driver and Method for Their Use," issued on Mar. 24, 2015, which is incorporated by reference herein in its entirety.

In some embodiments, the bone plate 80 is coupled to the plate inserter 60 by placing the fixation element 70 of the plate inserter 60 into the first fastener hole 94 of the bone plate 80. In some embodiments, the fixation element 70 includes threads configured to interface with the locking threads defined within the first fastener hole 94 to temporarily fix the bone plate 80 to the plate inserter 60. Although embodiments are illustrated including a threaded fixation element 70, it will be appreciated that any suitable fixation element can be used to releasably couple the bone plate 80 to the plate inserter 60.

Figure 10:
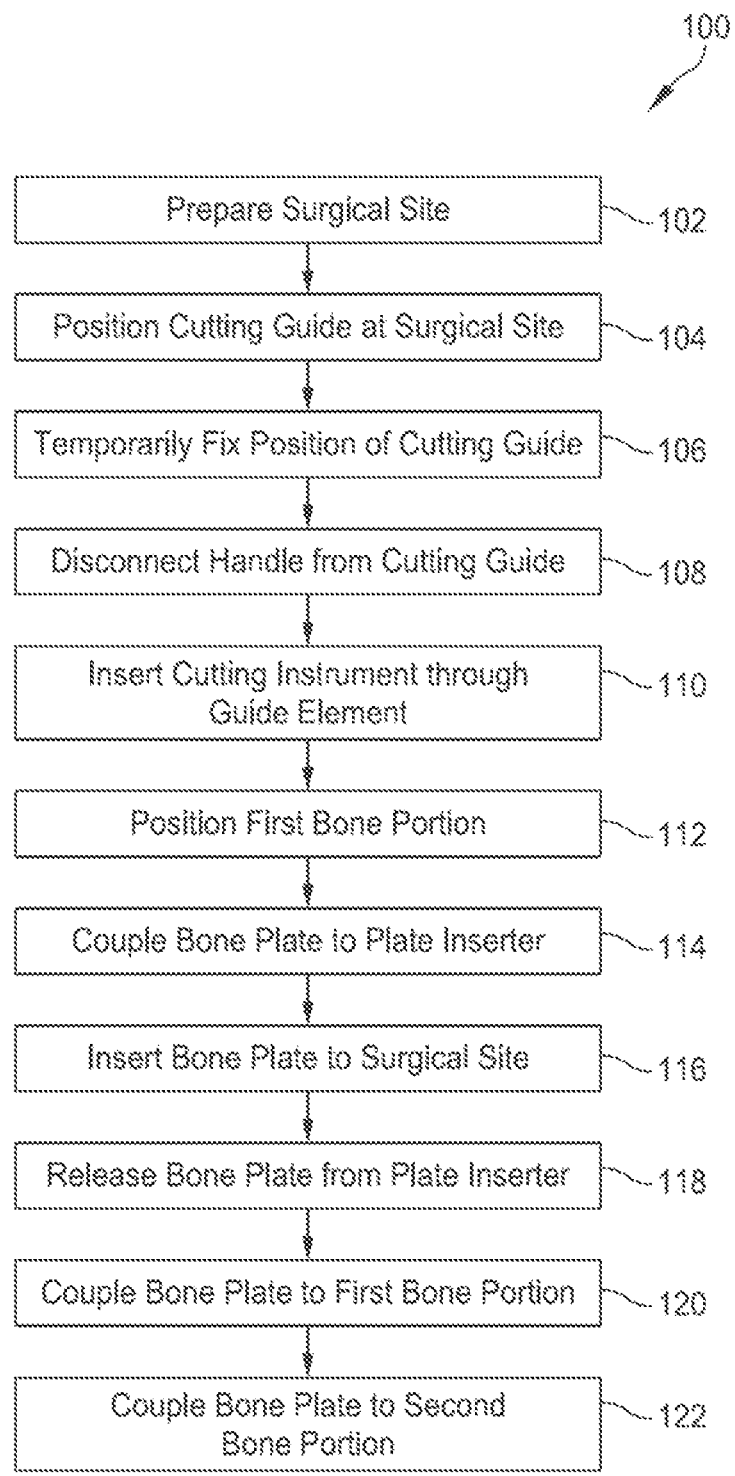
FIG. 10 is a flowchart illustrating a method of forming an osteotomy in a bone, in accordance with some embodiments.

FIG. 10 illustrates a method 100 of forming an osteotomy in a bone using the cutting guide 2 and plate inserter 60 described above. FIGS. 11-18 illustrate various steps of the method 100, in accordance with some embodiments. With reference to FIGS. 11-19, the method 100 is described. At step 102, a surgical site 200 is prepared for insertion of a cutting instrument. For example, in some embodiments, a surgical site 200 including at least a first bone 202 is positioned in a first predefined position. An incision is formed at a surgical site 200 adjacent to a first bone 202. The incision can be formed using any suitable surgical technique for forming an incision. In some embodiments, additional tissue, nerves, etc. may be separated from the first bone and/or otherwise positioned to facilitate additional steps of the method 100.

Figure 12:
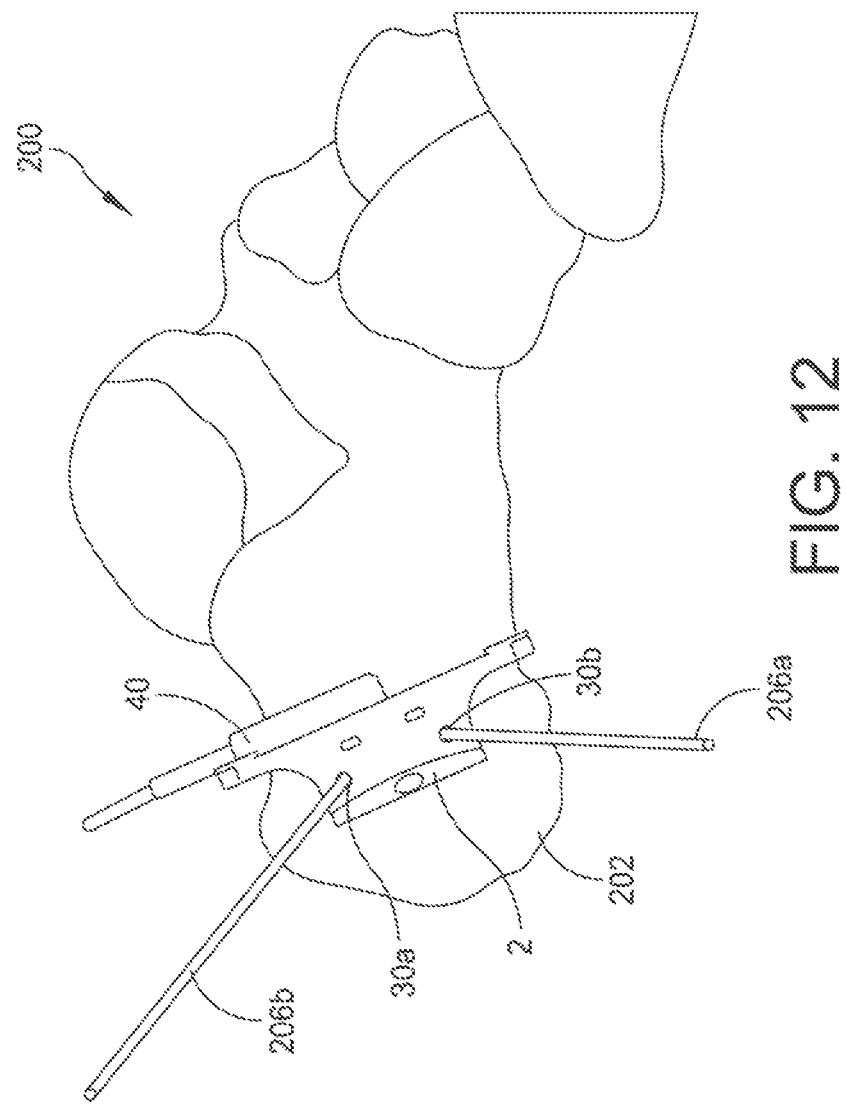
FIG. 12 illustrates the cutting guide of FIG. 11 coupled to the first bone by a first fixation device and a second fixation device, in accordance with some embodiments.

At step 104, a cutting guide 2a is positioned within the surgical site 200 and adjacent to the first bone 202, as illustrated in FIG. 12. Although FIG. 12 illustrates the cutting guide 2a being positioned immediately adjacent to the first bone 202, it will be appreciated that this is shown only for clarity, and that the cutting guide 2a can be positioned adjacent to the first bone 202 and abutting one or more tissue layers, such as muscle, skin, etc. positioned between the cutting guide 2a and the first bone 202. The cutting guide 2a is positioned such that a guide foot 10 contacts the first bone 202 (or tissue adjacent to the first bone 202) and such that the upper surface 12 of the cutting guide 2a is parallel to an intended osteotomy line. In some embodiments, the upper surface 12 is offset from the intended osteotomy line by a predetermined distance, such as, for example, a lateral offset.

In some embodiments, the position of the cutting guide 2a can be verified via imaging, such as fluoroscopy. For example, in some embodiments, the cutting guide 2a includes a plurality of alignment holes 36a, 36b extending through the body 4. The alignment holes 36a, 36b are configured to provide a fluoroscopic alignment indicator for ensuring proper alignment of the cutting guide 2a prior to fixing position of the cutting guide 2a. Although embodiments are discussed herein using fluoroscopic imaging, it will be appreciated that any suitable imaging may be used to verify alignment of the cutting guide 2a.

Figure 13:
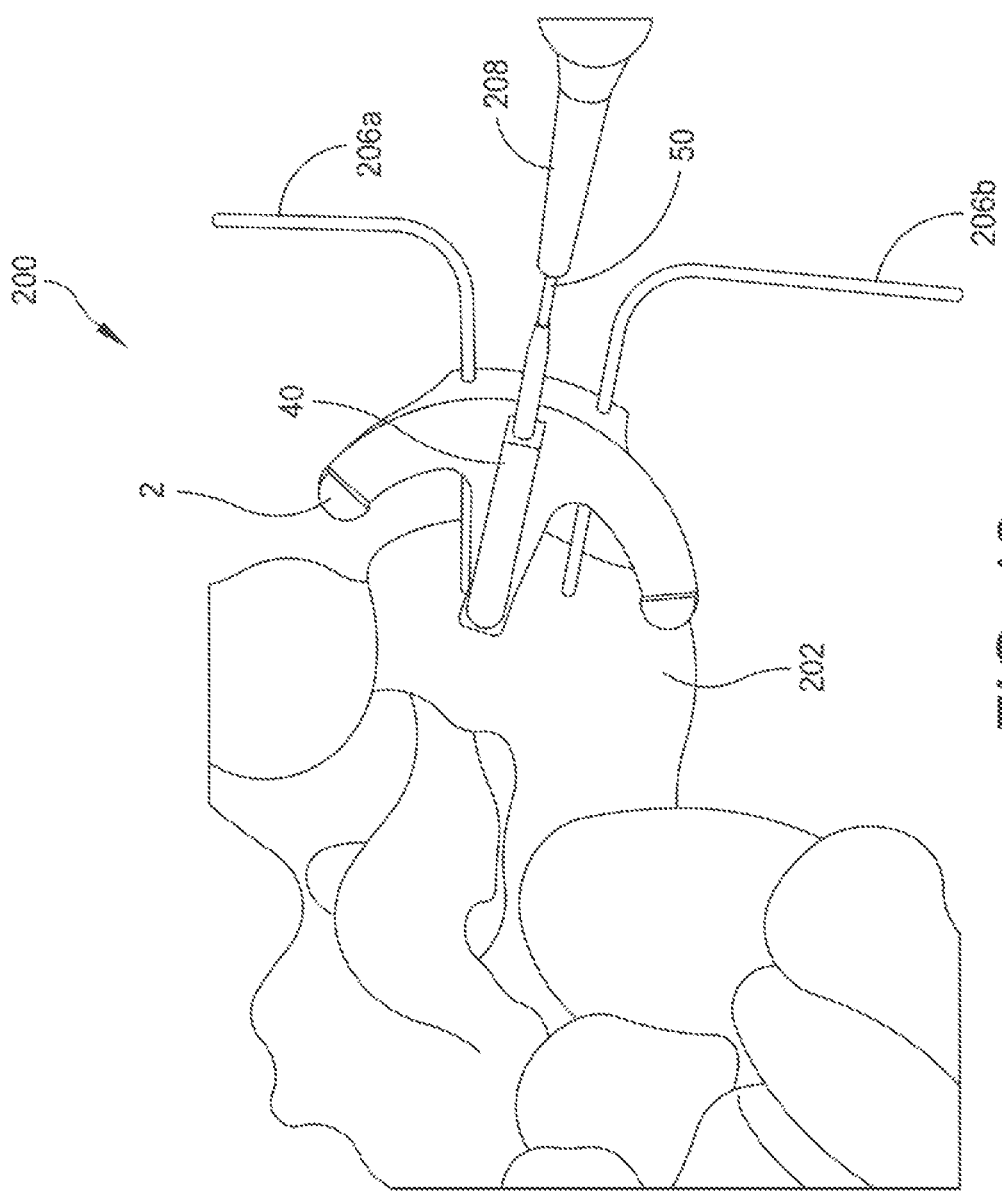
FIG. 13 illustrates a cutting instrument inserted through a pivoting guide portion of the cutting guide of FIG. 12, in accordance with some embodiments.

At step 106, a first temporary fixation device 206a and a second temporary fixation device 206b are inserted through first and second fixation holes 30a, 30b formed through the body 4 of the cutting guide 2a, as shown in FIG. 13.

Although an embodiment is illustrated including two temporary fixation devices 206a, 206b and two fixation holes 30a, 30b, it will be appreciated that the cutting guide 2a can include any number of fixation holes 30a, 30b and that any number of temporary fixation devices 206a, 206b may be used. As shown in FIG. 12, in some embodiments, the temporary fixation devices 206a, 206b can include k-wires, although it will be appreciated that any suitable temporary fixation device, such as k-wires, screws, nails, pins, etc., may be used. In embodiments including k-wires, the k-wires may be bent, cut, and/or otherwise manipulated to ensure proper access to the guide channel 44 defined by the guide element 40.

At step 108, the handle 20 is disconnected from the cutting guide 2a. The handle 20 may be disconnected from the body 4 using any suitable method, such as, for example, unthreading threads 24 defined on the handle 20 from threads defined in a hole 16a of the cutting guide 2a. In embodiments using other coupling mechanisms, such as slots, etc., the handle 20 can be removed from the cutting guide 2a using any suitable decoupling mechanism. In some embodiments, step 108 is omitted and the handle 20 is not removed from the cutting guide 2a. For example, the handle 20 may be removable but is not removed and/or may be permanently attached to the body 4 of the cutting guide 2a. For example, in an open procedure, the handle 20 may be permanently attached to the body.

Figure 14:
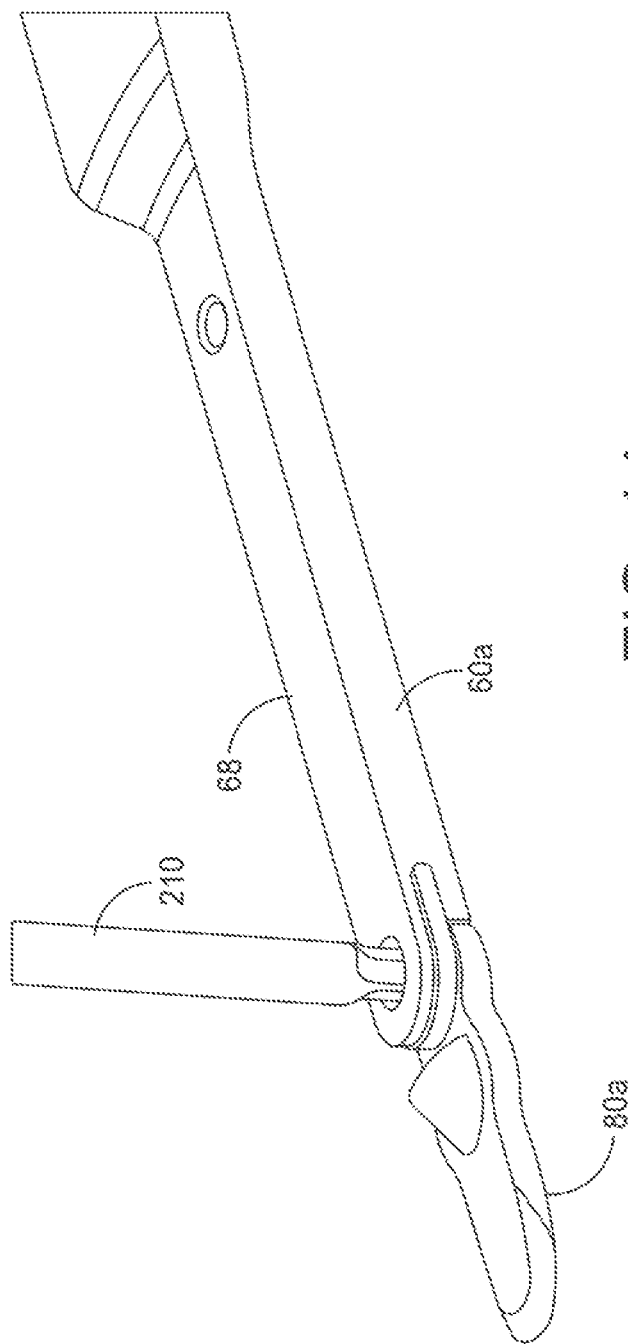
FIG. 14 illustrates a plate coupled to a plate inserter, in accordance with some embodiments.

At step 110, a cutting instrument 50a is inserted through the guide element 40 of the cutting guide 2a and is pivoted to form a cut (or osteotomy) in the first bone 202, as shown in FIG. 14. The cutting instrument 50a can include any suitable cutting instrument, such as a burr, drill bit, saw blade etc. The cutting instrument 50a can be coupled to a driver 208 configured to rotate the cutting instrument 50a. The guide element 40 and the cutting instrument 50a are pivoted about the pivot point defined by the pivoting element 46 coupled to the body 4. The cutting instrument 50a forms a cut in the first bone 202 in a plane defined by guide element 40. In some embodiments, the plane of the cut formed in the bone 202 is parallel to a plane defined by the upper surface 12 of the body 4. The guide element 40 allows the cutting instrument 50a to pivot in a first plane while preventing movement in any non-parallel direction with respect to the plane defined by the guide element 40, such as a plane parallel to the upper surface 12 of the body 4. The cutting instrument 50a separates the first bone 202 into a first portion 202a and a second portion 202b.

At step 112, the first portion 202a of the first bone 202 is moved and/or repositioned with respect to the second portion 202b. The first portion 202a can be moved in any suitable direction, such as, for example, medially, to correct one or more defects of the first bone 202. In some embodiments, the first portion 202a and/or the second portion 202b can be pinned and/or otherwise temporarily fixed to maintain the offset of the first portion 202a with respect to the second portion 202b.

At step 114, a bone plate 80a is coupled to a plate inserter 60a for insertion of the bone plate 80a to the surgical site 200, as shown in FIG. 14. The bone plate 80a can be coupled to the plate inserter 60a using any suitable coupling mechanism. For example, in the illustrated embodiment, the plate inserter 60a includes a rotatable coupling element 70 including a thread 71 configured to couple to a thread defined within a first fastener hole 94 defined by the bone plate 80a. The rotatable coupling element 70 can be coupled to the bone plate 80a by a driver 210. The driver can include any suitable driver configured to rotate the rotatable coupling element 70, such as a star driver, hex driver, etc.

Figure 15:
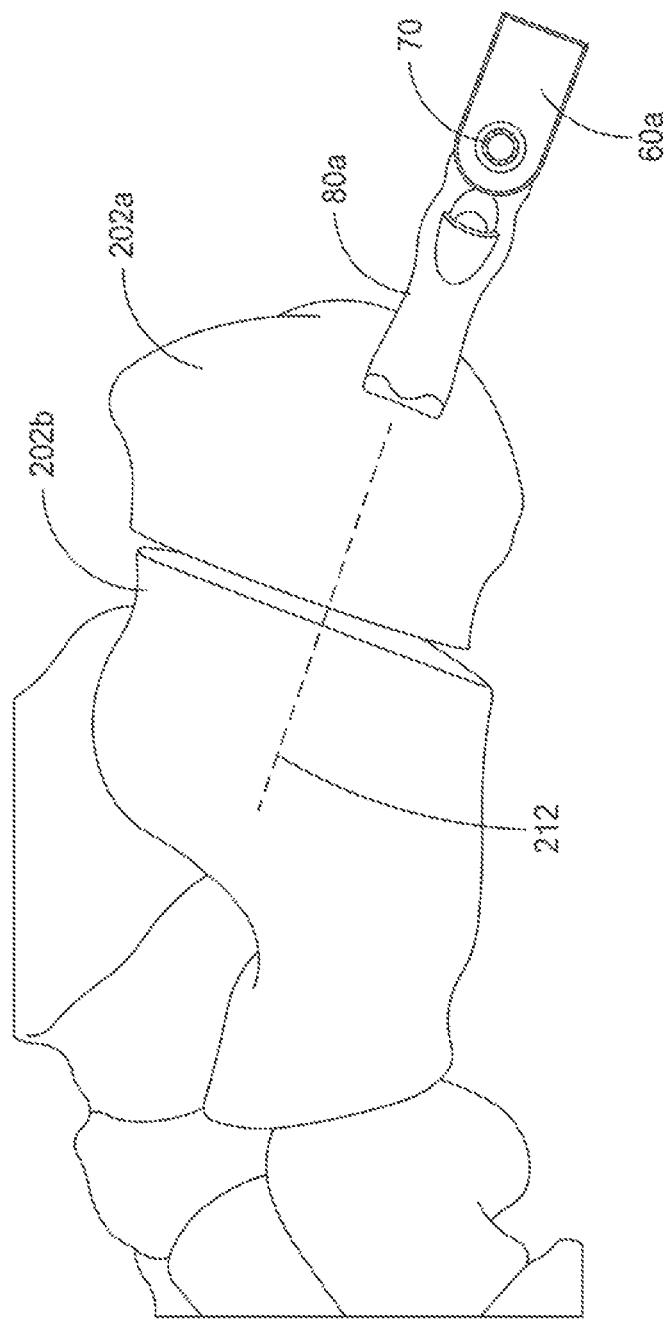
FIG. 15 illustrates a plate partially inserted with respect to a cut formed in the bone by the cutting instrument, in accordance with some embodiments.
Figure 16:
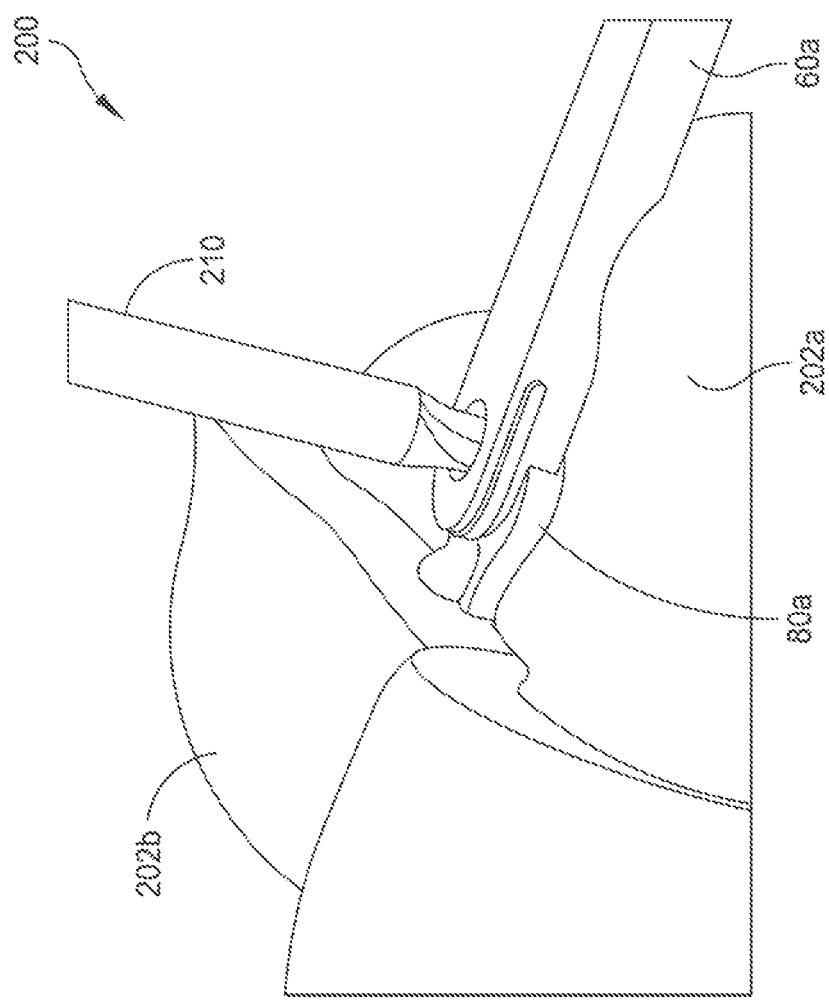
FIG. 16 illustrates a plate being separated from the plate inserter, in accordance with some embodiments.

At step 116, the bone plate 80a is inserted at the surgical site 200, as shown in FIGS. 15-16. In some embodiments, the bone plate 80a is inserted along a line 212 perpendicular to a plane defined by the osteotomy formed in the first bone 202. An insertion edge 90 and an insertion portion 92 are inserted into the second portion 202b of the first bone 202. The insertion portion 92 can be inserted up to any suitable depth, such as, for example, such that the hole shroud 98 is partially inserted into the second portion 202b of the first bone 202. The bottom surface 88b of the bone plate 80a is positioned in contact with the first portion 202a of the first bone 202. A second incision may be formed at the surgical site prior to insertion of the bone plate 80a. In some embodiments, a mallet or other striking instrument can be used to apply a force to a proximal end of the plate inserter 60a to facilitate insertion of the bone plate 80a into the second bone portion 202b. The bone plate 80a is in contact with an outer surface of the first bone portion 202a.

At step 118, the bone plate 80a is released from the plate inserter 60a. For example, as shown in FIG. 16, in some embodiments the driver 210 is coupled to the rotatable coupling element 70. The rotatable coupling element 70 is rotated to release the threads 71 from the first fastener hole 94 of the bone plate 80a, although it will be appreciated that any suitable release mechanism can be used based on the coupling between the bone plate 80a and the plate inserter 60a.

Figure 17:
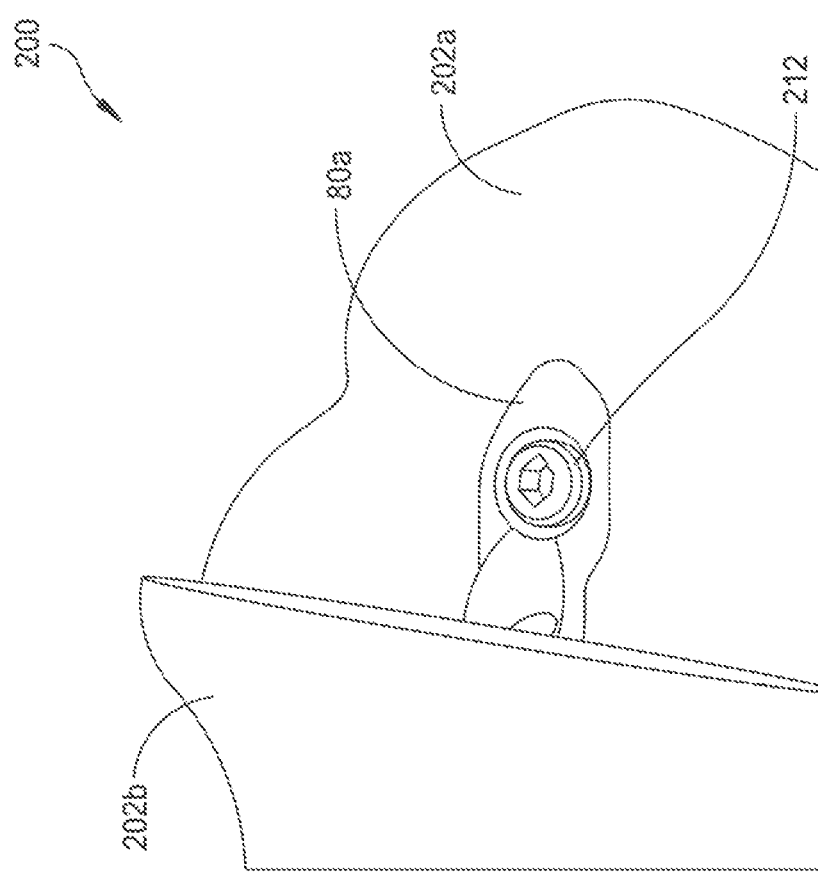
FIG. 17 illustrates a plate coupled to a first portion of the first bone, in accordance with some embodiments.

At step 120, the bone plate 80a is coupled to the first portion 202a of the first bone 202 by inserting a first fastener 212 through the first fastener hole 94 in the bone plate 80a, as shown in FIG. 17. In some embodiments, the first fastener 212 is a locking fastener configured to lock the bone plate 80a to a fixed position with respect to the first bone portion 202a. The first fastener 212 can include any suitable fastener, such as a polyaxial locking fastener. In some embodiments, a guide hole or pilot hole may be formed in the first bone portion 202a prior to insertion of the first fastener 212. The guide hole can be formed using any suitable instruments, such as, for example, a drill guide configured to be coupled to the first fastener hole 94 defined by the bone plate 80a.

Figure 18:
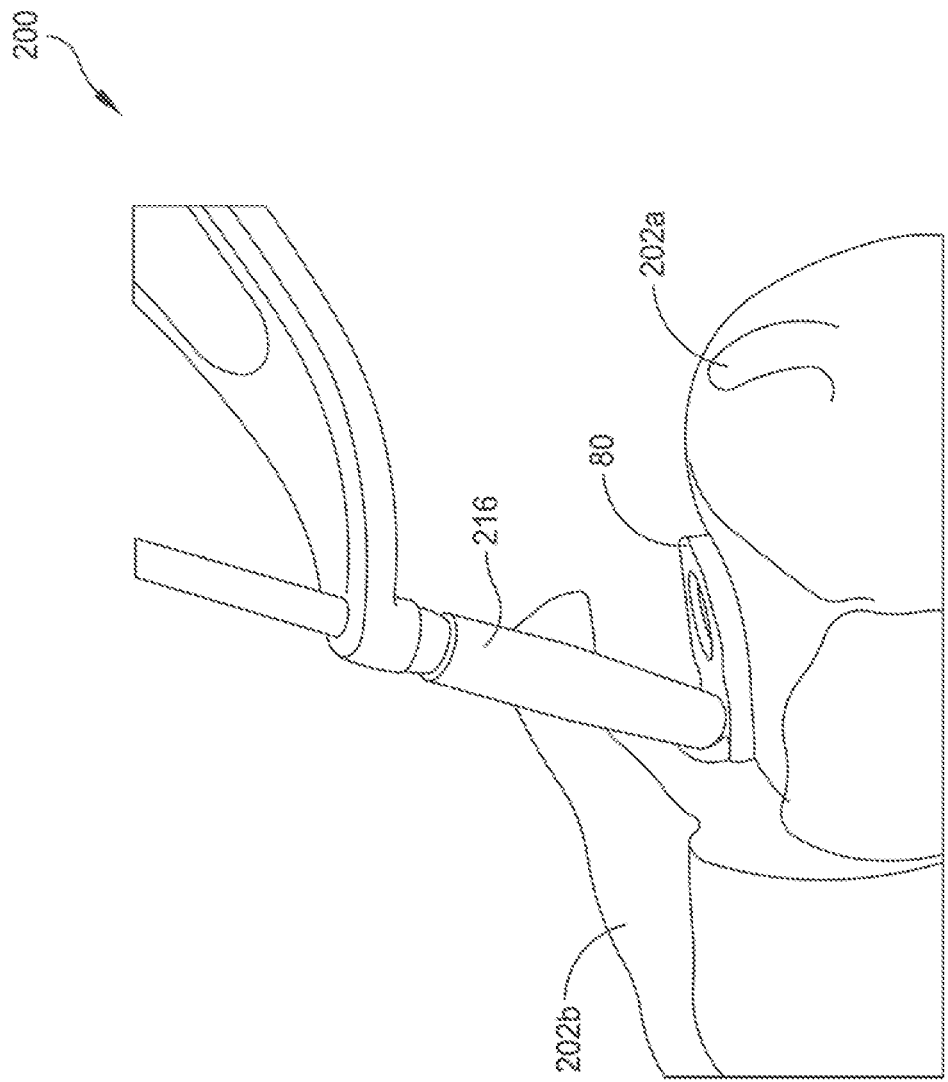
FIG. 18 illustrates a step of coupling a plate to a second portion of the first bone, in accordance with some embodiments.
Figure 19:
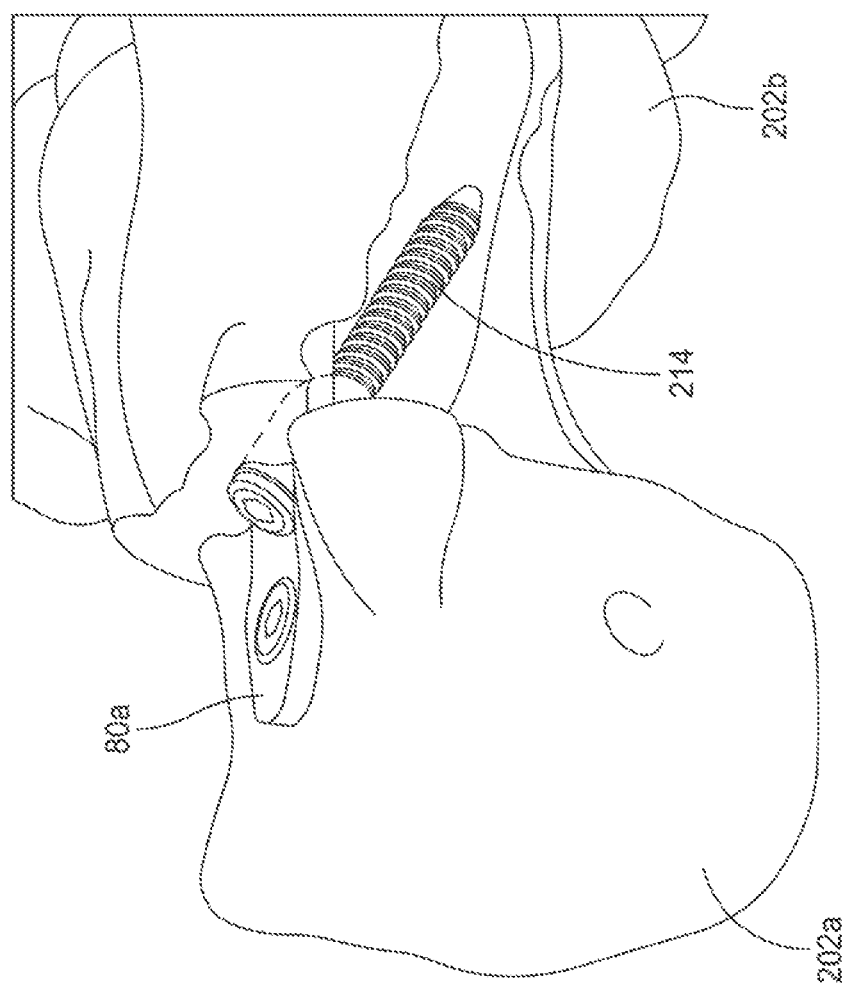
FIG. 19 illustrates a cross-section of the second bone portion including a second fastener coupling the bone plate to the second bone portion, in accordance with some embodiments.
Figure 21:
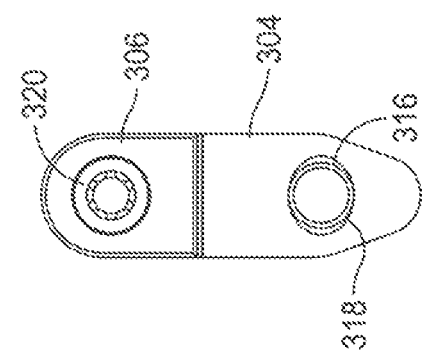
FIG. 21 illustrates a front view of the offset adapter of FIG. 20, in accordance with some embodiments.
Figure 23:
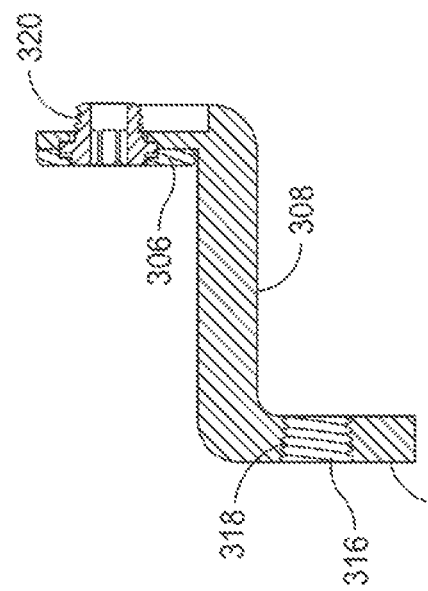
FIG. 23 illustrates a cross-section taken along line A-A of FIG. 21, in accordance with some embodiments.
Figure 20:
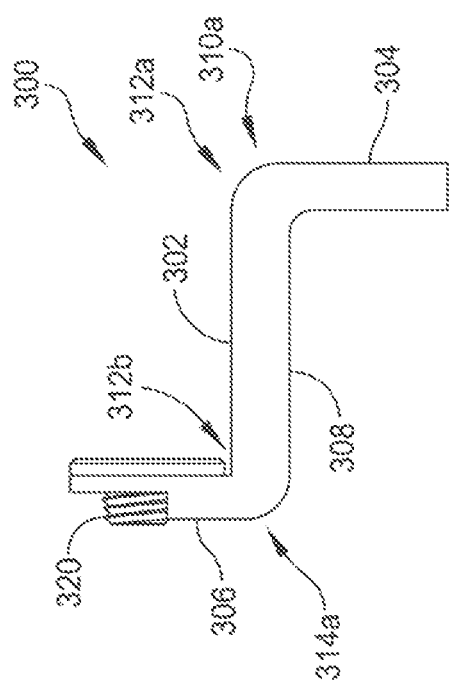
FIG. 20 illustrates a side view of an offset adapter configured to be coupled between a plate and a plate inserter, in accordance with some embodiments.
Figure 22:
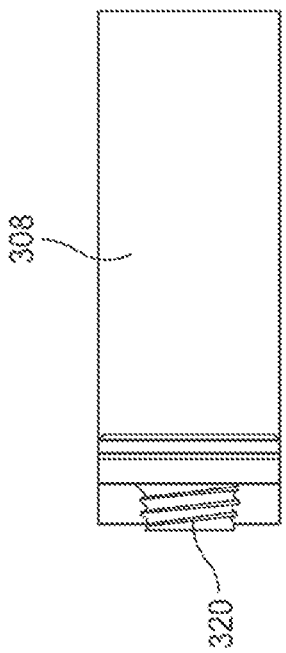
FIG. 22 illustrates a top view of the offset adapter of FIG. 20, in accordance with some embodiments.

At step 122, the bone plate 80a is coupled to the second bone portion 202b by inserting a second fastener 214 through the second fastener hole 96 defined in the bone plate 80a. The second fastener 212 can include a non-locking compression fastener configured to compress the first bone portion 202a and the second portion 202b, a locking compression fastener, and/or any other appropriately configured fastener. As shown in FIG. 18, in some embodiments, a guide hole or pilot hole may be formed in the second bone portion 202b prior to insertion of the second fastener 214. The guide hole can be formed using any suitable instruments, such as, for example, a drill guide 216 configured to be inserted partially into the second fastener hole 96 defined by the bone plate 80a. As shown in FIG. 19, the second fastener 214 extends into the second portion 202b of the first bone 202 to fix and compress the first bone portion 202a with respect to the second bone portion 202b.

FIGS. 20-23 illustrate an offset coupler 300 configured to couple a bone plate 80 to a plate inserter 60 in an offset position, in accordance with some embodiments. The offset coupler 300 includes a body 302 defining an inserter coupling portion 304, a plate coupling portion 306, and an offset portion 308. The inserter coupling portion 304 and the plate coupling portion 306 define planes having a predetermined and/or adjustable relationship. For example, in some embodiments, the inserter coupling portion 304 and the plate coupling portion 306 define parallel planes, although it will be appreciated that the inserter coupling portion 304 and the plate coupling portion 306 can define non-parallel planes. In some embodiments, the bone plate 80 is offset by one or more of a height offset, angle offset, and/or any other suitable offset (including fixed and/or adjustable offsets).

A first end 310a of the inserter coupling portion 304 is coupled to a first end 312a of the offset portion 308 and a first end 314a of the plate coupling portion 306 is coupled to a second end 312b of the offset portion 308. The offset portion 308 extends between the inserter coupling portion 304 and the plate coupling portion 306 at a predetermined angle with respect at least one of the planes defined by the inserter coupling portion 304 and the plate coupling portion 306. For example, in the illustrated embodiment, the offset portion 308 extends perpendicular to a plane defined by each of the inserter coupling portion 304 and the plate coupling portion 306, although it will be appreciated that the offset portion 308 can extend at a non-perpendicular angle with respect to a plane defined by either of the inserter coupling portion 304 and the plate coupling portion 306.

The inserter coupling portion 304 defines an coupling hole 316 extending therethrough. The coupling hole 316 is similar to the first fastener hole 94 defined in a bone plate 80 and is configured to couple the offset coupler 300 to the coupling element 70 of a plate inserter 60. The coupling hole 316 can include a complementary coupling element, such as a thread 318 complementary to a thread 71 formed on the coupling element 70. The coupling hole 316 is configured to fixedly couple the offset coupler 300 to the plate inserter 60.

In some embodiments, the plate coupling portion 306 includes a coupling element 320 configured to couple the plate coupling portion 306 to a bone plate 80. The coupling element 320 is substantially similar to the coupling element 70 of the plate inserter 60. For example, in embodiments including a plate inserter 60 having a threaded coupling element 70, the coupling element 320 is a threaded coupling element having a substantially similar thread configured to couple the coupling element 320 to a thread defined in a first fastener hole 94 of a bone plate 80. In embodiments including alternative coupling elements 70, the coupling element 320 provides similar coupling between the bone plate 80 and the plate coupling portion 306.

Figure 24:
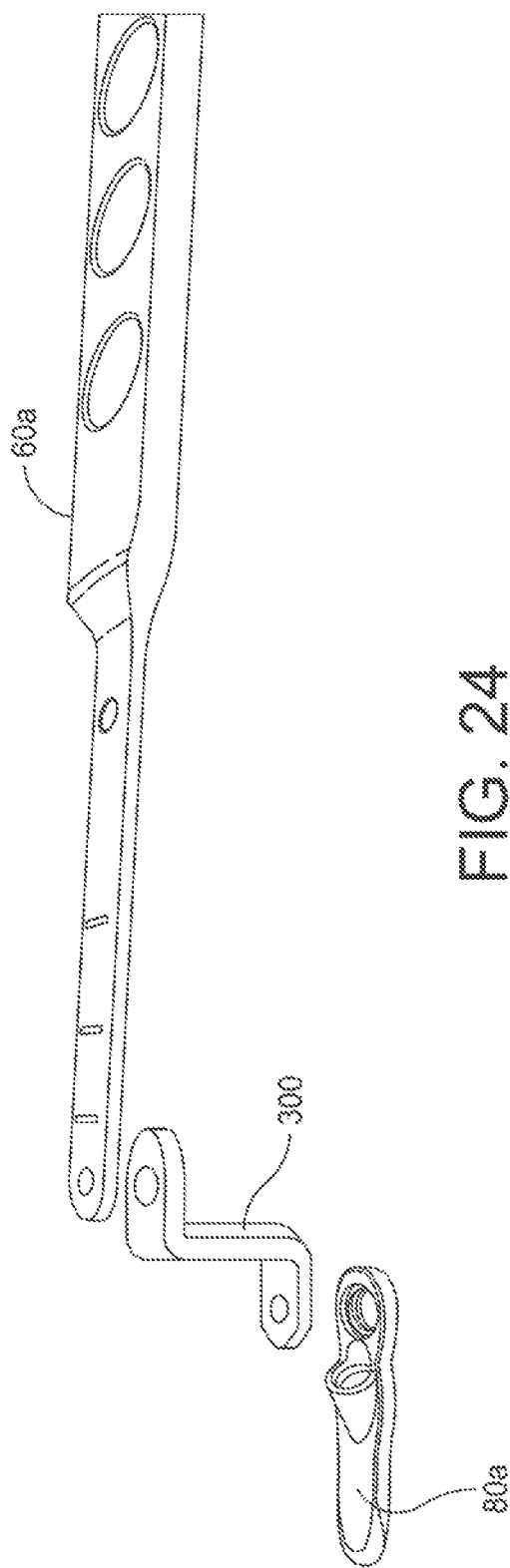
FIG. 24 illustrates a plate, offset adapter, and plate inserter, in accordance with some embodiments.

As shown in FIG. 24, the offset coupler 300 is configured to couple a bone plate 80a to a plate inserter 60a at an offset position. In some embodiments, the bone plate 80a is offset from the plate inserters 60a along an axis perpendicular to the longitudinal axes of the plate inserter 60a and the bone plate 80a. For example, in the illustrated embodiment, the bone plate 80a is offset from the plate inserter 60a by a distance equal to the thickness of each of the coupling portions 304, 306 and a length of the offset portion 308. In other embodiments, the bone plate 80a can be offset from the plate inserter 60a by a greater and/or lesser amount depending on the angle of each of the coupling portions 304, 306 and/or the offset portion 308.

In some embodiments, the offset coupler 300 is configured to adapt the plate inserter 60 for use in one or more alternative surgical procedures. For example, in some embodiments, the offset coupler 300 is configured to position the bone plate 80a with respect to the plate inserter 60a for use in one or more alternative osteotomy formation procedures, such as, for example, a minimally invasive chevron osteotomy procedure, an open procedure, and/or any other suitable surgical procedure.

Although the subject matter has been described in terms of exemplary embodiments, it is not limited thereto. Rather, the appended claims should be construed broadly, to include other variants and embodiments, which may be made by those skilled in the art.

What is claimed is:

1. A cutting guide comprising:
   a body extending between an upper surface and a lower surface and defined by a perimeter and a guide foot having a contact surface;
   a guide element pivotably coupled to the guide foot defining an open ended channel sized to receive a cutting instrument to thereby form an osteotomy in a bone when the cutting instrument is pivoted about and through a pivot point, through a plane parallel to the upper surface, with the guide element while engaging bone; and
   a handle comprising a body extending from a first end to a second end, wherein a first end is configured to be coupled to the body.

2. The cutting guide of claim 1, wherein the handle is releasably coupled to the body.

3. The cutting guide of claim 2, wherein the body comprises a coupling feature configured to releasably couple the handle to the body.

4. The system of claim 3, wherein the handle comprises a first coupling feature and the body of the cutting guide defines a second coupling feature, and wherein the first coupling feature and the second coupling feature are configured to releasably couple the handle to the body of the cutting guide.

5. The system of claim 4, wherein the first coupling feature comprises a first thread and the second coupling feature comprises a second thread configured to engage the first thread.

6. The cutting guide of claim 1, wherein the guide element comprises a guide element body extending along a longitudinal axis and the open ended channel is substantially along the longitudinal axis, wherein the longitudinal axis extends at a predetermined angle with respect to the upper surface of the body.

7. The cutting guide of claim 6, wherein the channel is sized and configured to receive the cutting element therethrough, wherein the guide element is configured to pivot with respect to the body such that the cutting element traverses a plane having a predetermined angle with respect to the upper guide surface.

8. The cutting guide of claim 7, wherein the cutting element includes a first portion having a first diameter sized and configured to be received within the channel of the guide element and a second portion having a second diameter, wherein the second diameter is less than the first diameter.

9. The cutting guide of claim 4, wherein the guide element comprises a projection extending from a first surface of the guide element body, wherein the projection is sized and configured to be received within a hole defined in the body of the cutting guide, and wherein the cutting guide body is configured to pivot about a pivot point defined by the hole.

10. The cutting guide of claim 1, wherein the body defines at least one fixation hole sized and configured to receive a fixation element therethrough.

* * * * *